US012245781B2

(12) United States Patent
Aklog et al.

(10) Patent No.: US 12,245,781 B2
(45) Date of Patent: *Mar. 11, 2025

(54) SYSTEMS AND METHODS FOR REMOVING UNDESIRABLE MATERIAL WITHIN A CIRCULATORY SYSTEM

(71) Applicant: AngioDynamics, Inc., Latham, NY (US)

(72) Inventors: Lishan Aklog, Scottsdale, AZ (US); Michael Glennon, Norwell, MA (US)

(73) Assignee: AngioDynamics, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/672,118

(22) Filed: May 23, 2024

(65) Prior Publication Data

US 2024/0366242 A1 Nov. 7, 2024

Related U.S. Application Data

(63) Continuation of application No. 18/390,932, filed on Dec. 20, 2023, which is a continuation of application (Continued)

(51) Int. Cl.
*A61B 17/22* (2006.01)
*A61B 17/3207* (2006.01)
(Continued)

(52) U.S. Cl.
CPC ........ *A61B 17/22* (2013.01); *A61B 17/22032* (2013.01); *A61B 17/3207* (2013.01);
(Continued)

(58) Field of Classification Search
CPC .. A61B 2017/22067; A61B 2017/2215; A61B 2217/005; A61B 2017/22079;
(Continued)

(56) References Cited

U.S. PATENT DOCUMENTS 1,050,030 A 1/1913 Keenan
3,831,587 A 8/1974 Boyd
(Continued)

FOREIGN PATENT DOCUMENTS

AU 2015274704 10/2016
AU 2016341439 5/2018
(Continued)

OTHER PUBLICATIONS

Behrens G, Bjarnason H. Venous Thromboembolic Disease: The Use of the Aspiration Thrombectomy Device AngioVac. Semin Intervent Radiol. 2015.

(Continued)

*Primary Examiner* — Leslie R Deak
(74) *Attorney, Agent, or Firm* — Kevin Radigan, Esq.; Heslin Rothenberg Farley & Mesiti P.C.

(57) ABSTRACT

A system is provided which includes a cannula and a secondary device. The cannula includes an expandable member, a cannula lumen, and a cannula proximal end. The expandable member includes a proximal most end, a distal most end, at least two movable sections, with the space between the at least two moveable sections, and an impermeable membrane extending across the space between each of the at least two moveable sections. In addition, the impermeable membrane extends from the expandable member distal most end to the expandable member proximal most end. The secondary device is configured to be coaxially placed through the cannula lumen. The cannula proximal end is configured to operatively couple to a vacuum source configured to create a negative pressure to pull an undesirable material into the cannula lumen.

20 Claims, 12 Drawing Sheets

Related U.S. Application Data

No. 16/667,060, filed on Oct. 29, 2019, now Pat. No. 11,896,246, which is a continuation of application No. 14/963,893, filed on Dec. 9, 2015, now Pat. No. 10,517,617, which is a continuation-in-part of application No. 13/940,299, filed on Jul. 12, 2013, now abandoned, which is a continuation-in-part of application No. 12/187,121, filed on Aug. 6, 2008, now Pat. No. 8,075,510.

(60) Provisional application No. 61/015,301, filed on Dec. 20, 2007.

(51) Int. Cl.
*A61M 1/00* (2006.01)
*A61M 1/36* (2006.01)

(52) U.S. Cl.
CPC . *A61M 1/3621* (2013.01); *A61B 2017/22034* (2013.01); *A61B 2017/22079* (2013.01); *A61B 2017/22094* (2013.01); *A61M 1/77* (2021.05); *A61M 1/79* (2021.05); *A61M 1/804* (2021.05); *A61M 1/84* (2021.05); *A61M 2205/7545* (2013.01)

(58) Field of Classification Search
CPC . A61B 17/22; A61B 2017/22034; A61F 2/01; A61M 1/0056; A61M 1/0058; A61M 1/3621; A61M 2205/7545
USPC ........ 604/4.01, 5.01, 6.09, 6.11, 6.16, 96.01, 604/103.07, 319; 606/200
See application file for complete search history.

(56) References Cited

U.S. PATENT DOCUMENTS

| | | | |
|---|---|---|---|
| 4,033,345 A | 7/1977 | Sorenson | |
| 4,046,150 A | 9/1977 | Schwartz | |
| 4,273,128 A | 6/1981 | Lary | |
| 4,437,856 A | 3/1984 | Valli | |
| 4,445,509 A | 5/1984 | Auth | |
| 4,469,100 A | 9/1984 | Hardwick | |
| 4,646,736 A | 3/1987 | Auth | |
| 4,664,112 A | 5/1987 | Kensey | |
| 4,671,796 A | 6/1987 | Groshong | |
| 4,681,564 A | 7/1987 | Landreneau | |
| 4,693,243 A | 9/1987 | Buras | |
| 4,696,667 A | 9/1987 | Masch | |
| 4,729,763 A | 3/1988 | Henrie | |
| 4,747,821 A | 5/1988 | Kensey | |
| 4,749,376 A | 6/1988 | Kensey | |
| 4,790,812 A | 12/1988 | Hawkins, Jr. | |
| 4,834,743 A | 5/1989 | Valerio | |
| 4,857,045 A | 8/1989 | Rydell | |
| 4,857,046 A | 8/1989 | Stevens | |
| 4,886,061 A | 12/1989 | Fischell | |
| 4,886,487 A | 12/1989 | Solem | |
| 4,892,529 A * | 1/1990 | Valerio ........... | A61M 1/02 604/319 |
| 4,895,166 A | 1/1990 | Farr | |
| 4,895,560 A | 1/1990 | Papantonakos | |
| 4,921,478 A | 5/1990 | Solano | |
| 4,990,134 A | 2/1991 | Auth | |
| 4,990,151 A | 2/1991 | Wallsten | |
| 5,011,488 A | 4/1991 | Ginsburg | |
| 5,019,089 A | 5/1991 | Farr | |
| 5,030,201 A | 7/1991 | Palestrant | |
| 5,055,198 A | 10/1991 | Shettigar | |
| 5,074,841 A | 12/1991 | Ademovic | |
| 5,078,677 A | 1/1992 | Gentelia | |
| 5,084,052 A | 1/1992 | Jacobs | |
| 5,092,839 A | 3/1992 | Kipperman | |
| 5,092,877 A | 3/1992 | Pinchuk | |
| 5,098,440 A | 3/1992 | Hillstead | |
| 5,100,376 A | 3/1992 | Blake, III | |
| 5,100,423 A | 3/1992 | Fearnot | |
| 5,102,415 A | 4/1992 | Guenther | |
| 5,114,399 A | 5/1992 | Kovalcheck | |
| 5,115,816 A | 5/1992 | Lee | |
| 5,133,703 A | 7/1992 | Boehringer | |
| 5,158,533 A | 10/1992 | Strauss | |
| 5,158,564 A | 10/1992 | Schnepp-Pesch | |
| 5,188,618 A | 2/1993 | Thomas | |
| 5,201,703 A | 4/1993 | Gentelia | |
| 5,211,651 A | 5/1993 | Reger | |
| 5,226,909 A | 7/1993 | Evans | |
| 5,234,403 A | 8/1993 | Yoda | |
| 5,242,441 A | 9/1993 | Avitall | |
| 5,257,974 A | 11/1993 | Cox | |
| 5,273,526 A | 12/1993 | Dance | |
| 5,306,250 A | 4/1994 | March | |
| 5,334,208 A | 8/1994 | Soehendra | |
| 5,380,314 A | 1/1995 | Herweck | |
| 5,423,799 A | 6/1995 | Shiu | |
| 5,464,408 A | 11/1995 | Duc | |
| 5,474,563 A | 12/1995 | Myler | |
| 5,490,859 A | 2/1996 | Mische | |
| 5,520,697 A | 5/1996 | Lindenberg | |
| 5,540,707 A | 7/1996 | Ressemann | |
| 5,569,275 A | 10/1996 | Kotula | |
| 5,571,086 A | 11/1996 | Kaplan | |
| 5,588,958 A | 12/1996 | Cunningham | |
| 5,628,746 A | 5/1997 | Clayman | |
| 5,632,755 A | 5/1997 | Nordgren | |
| 5,643,309 A | 7/1997 | Myler | |
| 5,653,684 A | 8/1997 | Laptewicz | |
| 5,695,489 A | 12/1997 | Japuntich | |
| 5,713,853 A | 2/1998 | Clark | |
| 5,722,964 A | 3/1998 | Herweck | |
| 5,733,302 A | 3/1998 | Myler | |
| 5,772,629 A | 6/1998 | Kaplan | |
| 5,776,141 A | 7/1998 | Klein | |
| 5,785,700 A | 7/1998 | Olson | |
| 5,785,715 A | 7/1998 | Schatz | |
| 5,788,661 A | 8/1998 | Japuntich | |
| 5,800,457 A | 9/1998 | Gelbfish | |
| 5,843,103 A | 12/1998 | Wulfman | |
| 5,846,251 A | 12/1998 | Hart | |
| 5,868,753 A | 2/1999 | Schatz | |
| 5,873,882 A | 2/1999 | Straub | |
| 5,908,435 A | 6/1999 | Samuels | |
| 5,910,144 A | 6/1999 | Hayashi | |
| 5,941,895 A | 8/1999 | Myler | |
| 6,001,112 A | 12/1999 | Taylor | |
| 6,059,745 A | 5/2000 | Gelbfish | |
| 6,083,239 A | 7/2000 | Addis | |
| 6,106,531 A | 8/2000 | Schatz | |
| 6,135,991 A | 10/2000 | Muni | |
| 6,159,220 A | 12/2000 | Gobron | |
| 6,159,230 A | 12/2000 | Samuels | |
| 6,161,547 A | 12/2000 | Barbut | |
| 6,187,016 B1 | 2/2001 | Hedges | |
| 6,200,276 B1 | 3/2001 | Biesel | |
| 6,203,537 B1 | 3/2001 | Adrian | |
| 6,206,868 B1 | 3/2001 | Parodi | |
| 6,206,898 B1 | 3/2001 | Honeycutt | |
| 6,241,738 B1 | 6/2001 | Dereume | |
| 6,274,055 B1 | 8/2001 | Zuk, Jr. | |
| 6,280,413 B1 | 8/2001 | Clark | |
| 6,280,464 B1 | 8/2001 | Hayashi | |
| 6,283,940 B1 | 9/2001 | Mulholland | |
| 6,287,321 B1 | 9/2001 | Jang | |
| 6,364,896 B1 | 4/2002 | Addis | |
| 6,394,978 B1 | 5/2002 | Boyle | |
| 6,413,235 B1 | 7/2002 | Parodi | |
| 6,423,032 B2 | 7/2002 | Parodi | |
| 6,443,966 B1 | 9/2002 | Shiu | |
| 6,451,036 B1 | 9/2002 | Heitzmann | |
| 6,454,775 B1 | 9/2002 | Demarais | |
| 6,454,779 B1 | 9/2002 | Taylor | |
| 6,491,712 B1 | 12/2002 | O'Connor | |
| 6,500,191 B2 | 12/2002 | Addis | |

(56) References Cited

U.S. PATENT DOCUMENTS

| | | |
|---|---|---|
| 6,508,782 B1 | 1/2003 | Evans |
| 6,540,712 B1 | 4/2003 | Parodi |
| 6,547,754 B1 | 4/2003 | Evans |
| 6,558,341 B1 | 5/2003 | Swisher |
| 6,569,181 B1 | 5/2003 | Burns |
| 6,582,396 B1 | 6/2003 | Parodi |
| 6,592,606 B2 | 7/2003 | Huter |
| 6,602,264 B1 | 8/2003 | McGuckin, Jr. |
| 6,660,014 B2 | 12/2003 | Demarais |
| 6,666,874 B2 | 12/2003 | Heitzmann |
| 6,673,039 B1 | 1/2004 | Bridges |
| 6,676,692 B2 | 1/2004 | Rabkin |
| 6,679,893 B1 | 1/2004 | Tran |
| 6,682,656 B2 | 1/2004 | Rothman |
| 6,685,722 B1 | 2/2004 | Rosenbluth |
| 6,695,858 B1 | 2/2004 | Dubrul |
| 6,702,830 B1 | 3/2004 | Demarais |
| 6,719,717 B1 | 4/2004 | Johnson |
| 6,749,619 B2 | 6/2004 | Ouriel |
| 6,776,770 B1 | 8/2004 | Trerotola |
| 6,802,846 B2 | 10/2004 | Hauschild |
| 6,808,520 B1 | 10/2004 | Fourkas |
| 6,808,531 B2 | 10/2004 | Lafontaine |
| 6,837,901 B2 | 1/2005 | Rabkin |
| 6,852,280 B2 | 2/2005 | Vijay |
| 6,878,153 B2 | 4/2005 | Linder |
| 6,905,490 B2 | 6/2005 | Parodi |
| 6,908,474 B2 | 6/2005 | Hogendijk |
| 6,936,060 B2 | 8/2005 | Hogendijk |
| 6,939,362 B2 | 9/2005 | Boyle |
| 6,945,977 B2 | 9/2005 | Demarais |
| 6,946,099 B2 | 9/2005 | Venkataramana |
| 6,960,222 B2 | 11/2005 | Vo |
| 6,962,598 B2 | 11/2005 | Linder |
| 7,014,913 B2 | 3/2006 | Pacetti |
| 7,063,707 B2 | 6/2006 | Bose |
| 7,108,704 B2 | 9/2006 | Trerotola |
| 7,118,585 B2 | 10/2006 | Addis |
| 7,153,292 B2 | 12/2006 | Morris |
| 7,153,320 B2 | 12/2006 | Euteneuer |
| 7,172,610 B2 | 2/2007 | Heitzmann |
| 7,175,660 B2 | 2/2007 | Cartledge |
| 7,220,269 B1 | 5/2007 | Ansel |
| 7,223,253 B2 | 5/2007 | Hogendijk |
| 7,229,402 B2 | 6/2007 | Diaz |
| 7,235,088 B2 | 6/2007 | Pintor |
| 7,258,696 B2 | 8/2007 | Rabkin |
| 7,300,458 B2 | 11/2007 | Henkes |
| 7,309,334 B2 | 12/2007 | Von Hoffmann |
| 7,344,549 B2 | 3/2008 | Boyle |
| 7,351,255 B2 | 4/2008 | Andreas |
| 7,353,956 B2 | 4/2008 | Lynn |
| 7,374,560 B2 | 5/2008 | Ressemann |
| 7,429,325 B2 | 9/2008 | Ingvarsson |
| 7,479,147 B2 | 1/2009 | Honeycutt |
| 7,655,016 B2 | 2/2010 | Demarais |
| 7,674,237 B2 | 3/2010 | O'Mahony et al. |
| 7,678,130 B2 | 3/2010 | Mazzocchi |
| 7,682,563 B2 | 3/2010 | Carpenter |
| 7,713,227 B2 | 5/2010 | Wholey |
| 7,766,934 B2 | 8/2010 | Pal |
| 7,771,445 B2 | 8/2010 | Heitzmann |
| 7,771,452 B2 | 8/2010 | Pal |
| 7,776,062 B2 | 8/2010 | Besselink |
| 7,780,696 B2 | 8/2010 | Daniel |
| 7,794,420 B2 | 9/2010 | Perovitch |
| 7,799,046 B2 | 9/2010 | White |
| 7,842,010 B2 | 11/2010 | Bonnette |
| 7,842,055 B2 | 11/2010 | Pintor |
| 7,862,575 B2 | 1/2011 | Tal |
| 7,879,022 B2 | 2/2011 | Bonnette |
| 7,892,273 B2 | 2/2011 | George |
| 7,896,832 B2 | 3/2011 | Zafirelis |
| 7,912,531 B1 | 3/2011 | Chiu |
| 7,938,820 B2 | 5/2011 | Webster |
| 8,034,095 B2 | 10/2011 | Randolph |
| 8,038,704 B2 | 10/2011 | Sherburne |
| 8,075,510 B2 | 12/2011 | Aklog |
| 8,167,903 B2 | 5/2012 | Hardert |
| 8,182,508 B2 | 5/2012 | Magnuson |
| 8,187,465 B2 | 5/2012 | Nierich |
| 8,216,269 B2 | 7/2012 | Magnuson |
| 8,298,252 B2 | 10/2012 | Krolik |
| 8,317,859 B2 | 11/2012 | Snow |
| 8,361,095 B2 | 1/2013 | Osborne |
| 8,377,092 B2 | 2/2013 | Magnuson |
| 8,469,970 B2 | 6/2013 | Diamant |
| 8,470,016 B2 | 6/2013 | Sherburne |
| 8,475,487 B2 | 7/2013 | Bonnette |
| 8,480,702 B2 | 7/2013 | Kusleika |
| 8,586,324 B2 | 11/2013 | Leach |
| 8,613,717 B2 * | 12/2013 | Aklog .............. A61B 17/22032 604/6.11 |
| 8,632,584 B2 | 1/2014 | Henkes |
| 8,734,374 B2 | 5/2014 | Aklog |
| 8,777,976 B2 | 7/2014 | Brady |
| 8,777,977 B2 | 7/2014 | Angel |
| 8,784,434 B2 | 7/2014 | Rosenbluth |
| 8,784,441 B2 | 7/2014 | Rosenbluth |
| 8,828,073 B2 | 9/2014 | Sherburne |
| 8,852,205 B2 | 10/2014 | Brady |
| 8,945,141 B2 | 2/2015 | Cahill |
| 8,945,170 B2 | 2/2015 | Paul, Jr. |
| 8,968,330 B2 | 3/2015 | Rosenbluth |
| 9,149,279 B2 | 10/2015 | Paul, Jr. |
| 9,149,609 B2 | 10/2015 | Ansel |
| 9,259,237 B2 | 2/2016 | Quick |
| 9,301,769 B2 | 4/2016 | Brady |
| 9,350,021 B2 | 5/2016 | Ohira |
| 9,351,749 B2 | 5/2016 | Brady |
| 9,351,861 B2 | 5/2016 | Sherburne |
| 9,393,035 B2 | 7/2016 | Yu |
| 9,402,707 B2 | 8/2016 | Brady |
| 9,408,620 B2 | 8/2016 | Rosenbluth |
| 9,439,661 B2 | 9/2016 | Johnson |
| 9,445,829 B2 | 9/2016 | Brady |
| 9,456,834 B2 | 10/2016 | Folk |
| 9,463,036 B2 | 10/2016 | Brady |
| 9,492,263 B2 | 11/2016 | Krolik |
| 9,526,864 B2 | 12/2016 | Quick |
| 9,526,865 B2 | 12/2016 | Quick |
| 9,579,116 B1 | 2/2017 | Nguyen |
| 9,642,635 B2 | 5/2017 | Vale |
| 9,642,639 B2 | 5/2017 | Brady |
| 9,700,332 B2 | 7/2017 | Marchand |
| 9,717,519 B2 | 8/2017 | Rosenbluth |
| 9,801,643 B2 | 10/2017 | Hansen |
| 9,815,038 B2 | 11/2017 | Leach |
| 9,820,769 B2 | 11/2017 | Krolik |
| 9,844,387 B2 | 12/2017 | Marchand |
| 9,855,067 B2 | 1/2018 | Krolik |
| 9,855,071 B2 | 1/2018 | Shaltis |
| 9,907,899 B2 | 3/2018 | Kim |
| 10,004,531 B2 | 6/2018 | Rosenbluth |
| 10,016,206 B1 | 7/2018 | Yang |
| 10,034,680 B2 | 7/2018 | Brady |
| 10,039,900 B2 | 8/2018 | Di Palma |
| 10,045,790 B2 | 8/2018 | Cox |
| 10,080,575 B2 | 9/2018 | Brady |
| 10,098,651 B2 | 10/2018 | Marchand |
| 10,201,360 B2 | 2/2019 | Vale |
| 10,213,582 B2 | 2/2019 | Garrison |
| 10,226,598 B2 | 3/2019 | Chou |
| 10,238,406 B2 | 3/2019 | Cox |
| 10,265,086 B2 | 4/2019 | Vale |
| 10,278,717 B2 | 5/2019 | Brady |
| 10,285,720 B2 | 5/2019 | Gilvarry |
| 10,292,722 B2 | 5/2019 | Brady |
| 10,292,723 B2 | 5/2019 | Brady |
| 10,299,811 B2 | 5/2019 | Brady |
| 10,300,256 B2 | 5/2019 | Aboytes |
| 10,335,186 B2 | 7/2019 | Rosenbluth |
| 10,342,571 B2 | 7/2019 | Marchand |
| 10,349,960 B2 | 7/2019 | Quick |

(56) References Cited

U.S. PATENT DOCUMENTS

| | | |
|---|---|---|
| 10,357,265 B2 | 7/2019 | Brady |
| 10,363,054 B2 | 7/2019 | Vale |
| 10,390,849 B2 | 8/2019 | Kugler |
| 10,390,850 B2 | 8/2019 | Vale |
| 10,420,570 B2 | 9/2019 | Vale |
| 10,441,301 B2 | 10/2019 | Vale |
| 10,456,555 B2 | 10/2019 | Garrison |
| 10,500,330 B2 | 12/2019 | Schwarz |
| 10,517,617 B2 | 12/2019 | Aklog |
| 10,517,622 B2 | 12/2019 | Vale |
| 10,517,708 B2 | 12/2019 | Gorochow |
| 10,524,811 B2 | 1/2020 | Marchand |
| 10,569,066 B2 | 2/2020 | Hayakawa |
| 10,582,939 B2 | 3/2020 | Brady |
| 10,588,648 B2 | 3/2020 | Brady |
| 10,588,649 B2 | 3/2020 | Brady |
| 10,588,655 B2 | 3/2020 | Rosenbluth |
| 10,610,246 B2 | 4/2020 | Brady |
| 10,617,435 B2 | 4/2020 | Vale |
| 10,667,833 B2 | 6/2020 | Vale |
| 10,675,045 B2 | 6/2020 | Brady |
| 10,682,152 B2 | 6/2020 | Vale |
| 10,682,454 B2 | 6/2020 | Coulthard |
| 10,729,459 B2 | 8/2020 | Krolik |
| 10,743,894 B2 | 8/2020 | Brady |
| 10,743,907 B2 | 8/2020 | Bruzzi |
| 10,772,649 B2 | 9/2020 | Hansen |
| 10,779,852 B2 | 9/2020 | Bruzzi |
| 10,792,055 B2 | 10/2020 | Brady |
| 10,792,056 B2 | 10/2020 | Vale |
| 10,799,331 B2 | 10/2020 | Hauser |
| 10,806,559 B2 | 10/2020 | Bonnette |
| 10,813,663 B2 | 10/2020 | Bruzzi |
| 10,842,498 B2 | 11/2020 | Vale |
| 10,874,421 B2 | 12/2020 | Bruzzi |
| 10,898,215 B2 | 1/2021 | Horowitz |
| 10,912,577 B2 | 2/2021 | Marchand |
| 10,952,760 B2 | 3/2021 | Brady |
| 10,953,200 B2 | 3/2021 | Sharma |
| 10,959,749 B2 | 3/2021 | Hatta |
| 11,000,682 B2 | 5/2021 | Merritt |
| 11,026,708 B2 | 6/2021 | Marks |
| 11,026,709 B2 | 6/2021 | Greenhalgh |
| 11,051,928 B2 | 7/2021 | Casey |
| 11,058,445 B2 | 7/2021 | Cox |
| 11,058,451 B2 | 7/2021 | Marchand |
| 11,065,018 B2 | 7/2021 | Buck |
| 11,076,876 B2 | 8/2021 | Vale |
| 11,154,314 B2 | 10/2021 | Quick |
| 11,253,277 B2 | 2/2022 | Buck |
| 11,259,821 B2 | 3/2022 | Buck |
| 11,266,825 B2 | 3/2022 | Peter |
| 11,432,835 B2 | 9/2022 | Shaffer |
| 11,439,799 B2 | 9/2022 | Buck |
| 11,457,936 B2 | 10/2022 | Buck |
| 11,529,495 B2 | 12/2022 | Keating |
| 11,553,935 B2 | 1/2023 | Buck |
| 11,554,005 B2 | 1/2023 | Merritt |
| 11,559,382 B2 | 1/2023 | Merritt |
| 11,607,478 B2 | 3/2023 | Gadrat |
| 11,633,272 B2 | 4/2023 | Buck |
| 11,642,209 B2 | 5/2023 | Merritt |
| 11,883,570 B2 | 1/2024 | Yao |
| 2001/0011179 A1 | 8/2001 | Adams |
| 2001/0031981 A1 | 10/2001 | Evans |
| 2001/0044598 A1 | 11/2001 | Parodi |
| 2001/0049486 A1 | 12/2001 | Evans |
| 2002/0010487 A1 | 1/2002 | Evans |
| 2002/0058964 A1 | 5/2002 | Addis |
| 2002/0072764 A1 | 6/2002 | Sepetka |
| 2002/0087119 A1 | 7/2002 | Parodi |
| 2002/0120277 A1 | 8/2002 | Hauschild |
| 2002/0143387 A1 | 10/2002 | Soetikno |
| 2002/0151918 A1 | 10/2002 | Lafontaine |
| 2002/0151922 A1 | 10/2002 | Hogendijk |
| 2002/0161377 A1 | 10/2002 | Rabkin |
| 2002/0161427 A1 | 10/2002 | Rabkin |
| 2002/0165574 A1 | 11/2002 | Ressemann |
| 2002/0173815 A1 | 11/2002 | Hogendijk |
| 2002/0173819 A1 | 11/2002 | Leeflang |
| 2002/0188276 A1 | 12/2002 | Evans |
| 2003/0023204 A1 | 1/2003 | Vo |
| 2003/0055445 A1 | 3/2003 | Evans |
| 2003/0093112 A1 | 5/2003 | Addis |
| 2003/0149467 A1 | 8/2003 | Linder |
| 2003/0195537 A1 | 10/2003 | Dubrul |
| 2003/0199890 A1 | 10/2003 | Dubrul |
| 2003/0236533 A1 | 12/2003 | Wilson |
| 2004/0019310 A1 | 1/2004 | Hogendijk |
| 2004/0064179 A1 | 4/2004 | Linder |
| 2004/0082962 A1 | 4/2004 | Demarais |
| 2004/0102728 A1 | 5/2004 | Foster |
| 2004/0147939 A1 | 7/2004 | Rabkin |
| 2004/0176659 A1 | 9/2004 | Peng |
| 2004/0181237 A1 | 9/2004 | Forde |
| 2004/0210298 A1 | 10/2004 | Rabkin |
| 2004/0260333 A1 | 12/2004 | Dubrul |
| 2005/0004594 A1 | 1/2005 | Nool |
| 2005/0080431 A1 | 4/2005 | Levine |
| 2005/0080480 A1 | 4/2005 | Bolea |
| 2005/0177022 A1 | 8/2005 | Chu |
| 2006/0009785 A1 | 1/2006 | Maitland |
| 2006/0041228 A1 | 2/2006 | Vo |
| 2006/0041304 A1 | 2/2006 | Jang |
| 2006/0047266 A1 | 3/2006 | Elkins |
| 2006/0047300 A1 | 3/2006 | Eidenschink |
| 2006/0047301 A1 | 3/2006 | Ogle |
| 2006/0095015 A1 | 5/2006 | Hobbs |
| 2006/0129095 A1 | 6/2006 | Pinchuk |
| 2006/0189930 A1 | 8/2006 | Lary |
| 2006/0195138 A1 | 8/2006 | Goll |
| 2006/0200191 A1 | 9/2006 | Zadno-Azizi |
| 2006/0253145 A1 | 11/2006 | Lucas |
| 2006/0270974 A1 | 11/2006 | Goff |
| 2007/0027520 A1 | 2/2007 | Sherburne |
| 2007/0038241 A1 | 2/2007 | Pal |
| 2007/0118072 A1 | 5/2007 | Nash |
| 2007/0238917 A1 | 10/2007 | Peng |
| 2007/0239182 A1 | 10/2007 | Glines |
| 2008/0033482 A1 | 2/2008 | Kusleika |
| 2008/0041516 A1 | 2/2008 | Chiu |
| 2008/0065008 A1 | 3/2008 | Barbut |
| 2008/0103439 A1 | 5/2008 | Torrance |
| 2008/0249558 A1 | 10/2008 | Cahill |
| 2009/0018567 A1 | 1/2009 | Escudero |
| 2009/0054918 A1 | 2/2009 | Henson |
| 2009/0099581 A1 | 4/2009 | Kim |
| 2009/0137984 A1 | 5/2009 | Minnelli |
| 2009/0163846 A1 | 6/2009 | Aklog |
| 2009/0222035 A1 | 9/2009 | Schneiderman |
| 2009/0292307 A1 | 11/2009 | Razack |
| 2009/0306702 A1 | 12/2009 | Miloslavski |
| 2010/0030327 A1 | 2/2010 | Chatel |
| 2010/0057184 A1 | 3/2010 | Randolph |
| 2010/0274277 A1 | 10/2010 | Eaton |
| 2011/0009837 A1 | 1/2011 | Schreiner |
| 2011/0054504 A1 | 3/2011 | Porter |
| 2011/0160763 A1 | 6/2011 | Ferrera |
| 2011/0190806 A1 | 8/2011 | Wittens |
| 2011/0213290 A1 | 9/2011 | Chin |
| 2011/0213392 A1 | 9/2011 | Aklog |
| 2012/0016455 A1 | 1/2012 | Sherburne |
| 2012/0059309 A1 | 3/2012 | Di Palma |
| 2012/0059356 A1 | 3/2012 | Di Palma |
| 2012/0150193 A1 | 6/2012 | Aklog |
| 2012/0197277 A1 | 8/2012 | Stinis |
| 2012/0253358 A1 | 10/2012 | Golan |
| 2013/0090624 A1 | 4/2013 | Munsinger |
| 2013/0289694 A1 | 10/2013 | Sherburne |
| 2013/0304082 A1 | 11/2013 | Aklog |
| 2014/0074144 A1 | 3/2014 | Shrivastava |
| 2014/0155908 A1 | 6/2014 | Rosenbluth |
| 2014/0171958 A1 | 6/2014 | Baig |
| 2014/0296868 A1 | 10/2014 | Garrison |

(56) References Cited

U.S. PATENT DOCUMENTS

| | | |
|---|---|---|
| 2014/0324091 A1 | 10/2014 | Rosenbluth |
| 2014/0350591 A1 | 11/2014 | Sherburne |
| 2014/0364833 A1 | 12/2014 | Christensen |
| 2015/0018859 A1 | 1/2015 | Quick |
| 2015/0127044 A1 | 5/2015 | Cahill |
| 2015/0238207 A1 | 8/2015 | Cox |
| 2015/0305756 A1 | 10/2015 | Rosenbluth |
| 2015/0314057 A1 | 11/2015 | Labib |
| 2015/0352325 A1 | 12/2015 | Quick |
| 2015/0360001 A1 | 12/2015 | Quick |
| 2016/0008014 A1 | 1/2016 | Rosenbluth |
| 2016/0038174 A1 | 2/2016 | Bruzzi |
| 2016/0095744 A1 | 4/2016 | Wolfertz |
| 2016/0106353 A1 | 4/2016 | Schuetz |
| 2016/0143721 A1 | 5/2016 | Rosenbluth |
| 2016/0206344 A1 | 7/2016 | Bruzzi |
| 2016/0262790 A1 | 9/2016 | Rosenbluth |
| 2016/0287276 A1 | 10/2016 | Cox |
| 2017/0079672 A1 | 3/2017 | Quick |
| 2017/0105745 A1 | 4/2017 | Rosenbluth |
| 2017/0112513 A1 | 4/2017 | Marchand |
| 2017/0112514 A1 | 4/2017 | Marchand |
| 2017/0136158 A1 | 5/2017 | Culhane |
| 2017/0189041 A1 | 7/2017 | Cox |
| 2017/0265878 A1 | 9/2017 | Marchand |
| 2017/0325839 A1 | 11/2017 | Rosenbluth |
| 2017/0333076 A1 | 11/2017 | Bruzzi |
| 2018/0042623 A1 | 2/2018 | Batiste |
| 2018/0092652 A1 | 4/2018 | Marchand |
| 2018/0193043 A1 | 7/2018 | Marchand |
| 2018/0256178 A1 | 9/2018 | Cox |
| 2018/0271556 A1 | 9/2018 | Bruzzi |
| 2018/0296240 A1 | 10/2018 | Rosenbluth |
| 2018/0344339 A1 | 12/2018 | Cox |
| 2018/0361116 A1 | 12/2018 | Quick |
| 2019/0046219 A1 | 2/2019 | Marchand |
| 2019/0070401 A1 | 3/2019 | Merritt |
| 2019/0150959 A1 | 5/2019 | Cox |
| 2019/0184076 A1 | 6/2019 | Gourlay |
| 2019/0231373 A1 | 8/2019 | Quick |
| 2019/0321071 A1 | 10/2019 | Marchand |
| 2020/0030504 A1 | 1/2020 | Igarashi |
| 2020/0046368 A1 | 2/2020 | Merritt |
| 2020/0164117 A1 | 5/2020 | Culhane |
| 2020/0178991 A1 | 6/2020 | Greenhalgh |
| 2021/0022766 A1 | 1/2021 | Bruzzi |
| 2021/0093758 A1 | 4/2021 | Corrales |
| 2021/0113224 A1 | 4/2021 | Dinh |
| 2021/0186537 A1 | 6/2021 | Buck |
| 2021/0186812 A1 | 6/2021 | Pennie |
| 2021/0187244 A1 | 6/2021 | Buck |
| 2021/0315598 A1 | 10/2021 | Buck |
| 2021/0316127 A1 | 10/2021 | Buck |
| 2021/0402086 A1 | 12/2021 | Jokaji |
| 2022/0104839 A1 | 4/2022 | Horowitz |
| 2022/0104840 A1 | 4/2022 | Horowitz |
| 2022/0125456 A1 | 4/2022 | Horowitz |
| 2022/0184290 A1 | 6/2022 | Herzlinger |
| 2022/0226555 A1 | 7/2022 | Sunenshine |
| 2022/0240959 A1 | 8/2022 | Quick |
| 2022/0330960 A1 | 10/2022 | Buck |
| 2022/0346800 A1 | 11/2022 | Merritt |
| 2022/0346813 A1 | 11/2022 | Quick |
| 2022/0346814 A1 | 11/2022 | Quick |
| 2023/0015259 A1 | 1/2023 | Buck |
| 2023/0046775 A1 | 2/2023 | Quick |
| 2023/0062809 A1 | 3/2023 | Merritt |
| 2023/0233311 A1 | 7/2023 | Merritt |

FOREIGN PATENT DOCUMENTS

| | | |
|---|---|---|
| AU | 2018328011 | 3/2020 |
| AU | 2019321256 A1 | 3/2021 |
| CA | 2939315 | 12/2015 |
| CA | 3002154 | 4/2017 |
| CA | 3074564 | 3/2019 |
| CA | 3114285 A1 | 2/2020 |
| CN | 1278713 | 1/2001 |
| CN | 1486758 | 4/2004 |
| CN | 108472052 | 8/2018 |
| CN | 109069790 | 12/2018 |
| CN | 110312481 | 10/2019 |
| CN | 112867455 A | 5/2021 |
| EP | 0518975 B1 | 5/1997 |
| EP | 2897536 | 7/2015 |
| EP | 3094363 | 11/2016 |
| EP | 3364891 | 8/2018 |
| EP | 3389757 | 10/2018 |
| EP | 3528717 | 8/2019 |
| EP | 3836855 A4 | 8/2022 |
| EP | 3362116 B1 | 6/2023 |
| JP | H025976 | 1/1990 |
| JP | 2003521286 | 7/2003 |
| JP | 2006015058 | 1/2006 |
| JP | 2007319272 | 12/2007 |
| JP | 6438495 | 12/2018 |
| JP | 2018537229 | 12/2018 |
| JP | 2018538027 | 12/2018 |
| JP | 2021534851 A | 12/2021 |
| WO | 9945835 | 9/1999 |
| WO | 2005079678 A1 | 9/2005 |
| WO | 2006029270 A1 | 3/2006 |
| WO | 2006063199 | 6/2006 |
| WO | 2006100651 A1 | 9/2006 |
| WO | 2010119110 | 10/2010 |
| WO | 2011144336 | 11/2011 |
| WO | 2012156924 | 11/2012 |
| WO | 2014093845 A1 | 6/2014 |
| WO | 2014141226 | 9/2014 |
| WO | 2015071852 A2 | 5/2015 |
| WO | 2016067246 A1 | 5/2016 |
| WO | 2016071524 | 5/2016 |
| WO | 2017070702 | 4/2017 |
| WO | 2017106877 | 6/2017 |
| WO | 2019050765 | 3/2019 |
| WO | 2021076954 | 4/2021 |
| WO | 2022082213 | 4/2022 |

OTHER PUBLICATIONS

F.A.S.T. Funnel Catheter Proximal Occlusion Embolectomy/Thrombectomy System, Genesis Medical Interventional, 4 pages. (2008).

Greenfield et al., Transvenous Removal of Pulmonary Emboli by Vacuum-Cup Catheter Technique, Journal of Surgical Research, vol. 9, No. 6(Jun. 1969) pp. 347-352.

Hansman, Heather. "This Pump Could Make Blood Transfusions Safer and Cheaper in the Developing World." Smithsonian Magazine. Nov. 20, 2015, https://www.smithsonianmag.com/innovation/pump-could-make-blood-transfusions-safer-and-cheaper-developing-world-180957250/#:~:text=The%20Hemafuse%2C%20which%20looks%20like,where%20it%20can%20be%20retransfused (accessed Apr. 21, 2024).

International Search Report and Written Opinion for PCT/US2012/032291 mailed on Aug. 10, 2012, 14 pages.

International Search Report and Written Opinion for PCT/US2012/032295 mailed on Jul. 6, 2012, 13 pages.

International Search Report and Written Opinion for PCT/US2012/032306 mailed on Aug. 13, 2012, 12 pages.

International Search Report and Written Opinion for PCT/US2012/032311 mailed on Sep. 7, 2012, 14 pages.

International Search Report EP03252158_AESR dated Aug. 29, 2003, 1 page.

International Search Report EP08864356_SESR dated Apr. 1, 2014, 2 pages.

International Search Report PCT-NL-08-050399 ISR dated Feb. 13, 2009, 3 pages.

International Search Report PCT-US-08-072352 IPRP dated Nov. 4, 2008, 11 pages.

International Search Report PCT-US-12-032291 IPRP dated Aug. 10, 2012, 11 pages.

(56) References Cited

OTHER PUBLICATIONS

International Search Report PCT-US-12-032299 IPRP dated Oct. 2, 2012, 7 pages.
International Search Report PCT-US-12-032299 ISR dated Oct. 2, 2012, 3 pages.
International Search Report PCT-US-12-032299_WOSA dated Oct. 2, 2012, 6 pages.
International Search Report PCT-US-12-032306 IPRP dated Aug. 13, 2012, 6 pages.
International Search Report PCT-US-12-032306 ISR dated Aug. 13, 2012, 2 pages.
International Search Report PCT-US-12-032306_WOSA dated Aug. 13, 2012, 5 pages.
International Search Report PCT-US-12-032311 IPRP dated Sep. 7, 2012, 6 pages.
International Search Report PCT-US-12-032311_ISR dated Sep. 7, 2012, 4 pages.
International Search Report PCT-US-12-032311_WOSA dated Sep. 7, 2012, 5 pages.
Nael et al., Endovascular Management of Central Thoracic Veno-Occlusive Diseases in Hemodialysis Patients: A Single Institutional Experience in 69 Consecutive Patients, Journal of Vascular Interventional Radiology, vol. 20, No. 1, 2009, pp. 46-51.
Notice of Allowance dated May 21, 2024 for U.S. Appl. No. 16/778,657 (pp. 1-9).
Notice of Allowance dated Jun. 17, 2024 for U.S. Appl. No. 16/778,657 (pp. 1-2).
PCT International Search Report based on PCT/US2008/072352 dated Nov. 4, 2008, 1 page.
Sisu Global. "The Hemafuse." Jun. 2018, https://sisuglobal.health/hemafuse. (accessed Apr. 21, 2024).
Valji, et al, Pulsed-Spray Thrombolysis of Arterial and Bypass Graft Occlusion, American Roentgen Ray Society, pp. 617-621 (Mar. 1991).

\* cited by examiner

SYSTEMS AND METHODS FOR REMOVING UNDESIRABLE MATERIAL WITHIN A CIRCULATORY SYSTEM

CROSS REFERENCE TO RELATED APPLICATIONS

This application is a Continuation U.S. patent application Ser. No. 18/390,932, filed Dec. 20, 2023; which is a Continuation of U.S. patent application Ser. No. 16/667,060, filed Oct. 29, 2019, now U.S. Pat. No. 11,896,246, issued Feb. 13, 2024; which is a Continuation of U.S. application Ser. No. 14/963,893, filed Dec. 9, 2015, now U.S. Pat. No. 10,517,617, issued Dec. 31, 2019; which is a Continuation in-part of U.S. application Ser. No. 13/940,299, filed Jul. 12, 2013; which is a Continuation-in part of U.S. patent application Ser. No. 12/187,121, filed Aug. 6, 2008, now U.S. Pat. No. 8,075,510, issued Dec. 13, 2011; which claims the benefit of U.S. Provisional Application No. 61/015,301, filed Dec. 20, 2007, the content of all of which are hereby incorporated herein by reference in their entireties.

TECHNICAL FIELD

The present invention relates to systems and methods for removing undesirable materials from a site of interest within the circulatory system. More particularly, the present invention relates to systems and methods for removing substantially en bloc clots, thrombi, and emboli, among others, from within heart chambers, as well as medium to large vessels, while reinfusing fluid removed from the site of interest back into the patient to minimize fluid loss.

BACKGROUND ART

Many of the most common and deadly diseases afflicting mankind result from or in the presence of undesirable material, most notably blood clots, in the blood vessels and heart chambers. Examples of such diseases include myocardial infarction, stroke, pulmonary embolism, deep venous thrombosis, atrial fibrillation, infective endocarditis, etc. The treatment of some of these conditions, which involve smaller blood vessels, such as myocardial infarction and stroke, has been dramatically improved in recent years by targeted mechanical efforts to remove blood clots from the circulatory system. Other deadly conditions, which involve medium to large blood vessels or heart chambers, such as pulmonary embolism (½ million deaths per year) or deep venous thrombosis (2-3 million cases per year) have not benefited significantly from such an approach. Present treatment for such conditions with drugs or other interventions is not sufficiently effective. As a result, additional measures are needed to help save lives of patients suffering from these conditions.

The circulatory system can be disrupted by the presence of undesirable material, most commonly blood clots, but also tumors, infective vegetations, and foreign bodies, etc. Blood clots can arise spontaneously within the blood vessel or heart chamber (thrombosis) or be carried through the circulation from a remote site and lodge in a blood vessel (thromboemboli).

In the systemic circulation, this undesirable material can cause harm by obstructing a systemic artery or vein. Obstructing a systemic artery interferes with the delivery of oxygen-rich blood to organs and tissues (arterial ischemia) and can ultimately lead to tissue death or infarction. Obstructing a systemic vein interferes with the drainage of oxygen-poor blood and fluid from organs and tissues (venous congestion) resulting in swelling (edema) and can occasionally lead to tissue infarction.

Many of the most common and deadly human diseases are caused by systemic arterial obstruction. The most common form of heart disease, such as myocardial infarction, results from thrombosis of a coronary artery following disruption of a cholesterol plaque. The most common causes of stroke include obstruction of a cerebral artery either from local thrombosis or thromboemboli, typically from the heart. Obstruction of the arteries to abdominal organs by thrombosis or thromboemboli can result in catastrophic organ injury, most commonly infarction of the small and large intestine. Obstruction of the arteries to the extremities by thrombosis or thromboemboli can result in gangrene.

In the systemic venous circulation, undesirable material can also cause serious harm. Blood clots can develop in the large veins of the legs and pelvis, a common condition known as deep venous thrombosis (DVT). DVT arises most commonly when there is a propensity for stagnated blood (long-haul air travel, immobility) and clotting (cancer, recent surgery, especially orthopedic surgery). DVT causes harm by (1) obstructing drainage of venous blood from the legs leading to swelling, ulcers, pain and infection and (2) serving as a reservoir for blood clot to travel to other parts of the body including the heart, lungs (pulmonary embolism) and across an opening between the chambers of the heart (patent foramen *ovale*) to the brain (stroke) abdominal organs or extremities.

In the pulmonary circulation, the undesirable material can cause harm by obstructing pulmonary arteries, a condition known as pulmonary embolism. If the obstruction is upstream, in the main or large branch pulmonary arteries, it can severely compromise total blood flow within the lungs and therefore the entire body, resulting in low blood pressure and shock. If the obstruction is downstream, in large to medium pulmonary artery branches, it can prevent a significant portion of the lung from participating in the exchange of gases to the blood resulting low blood oxygen and build up of blood carbon dioxide. If the obstruction is farther downstream, it can cut off the blood flow to a smaller portion of the lung, resulting in death of lung tissue or pulmonary infarction.

The presence of the undesirable material within the heart chambers can cause harm by obstructing flow or by serving as a reservoir for emboli to other organs in the body. The most common site for obstruction within the heart is in the heart valves. Infective vegetations, a condition known as endocarditis, can cause partial obstruction to flow across a valve before destroying the valve. Patients with prosthetic valves, especially mechanical valves, are particularly prone to valve thrombosis and obstruction. The heart chambers are the most common source of emboli (cardioemboli) to the systemic circulation, including stroke. Emboli tend to arise from areas that are prone to stagnation of blood flow under pathologic conditions. The left atrial appendage in patients with atrial fibrillation is prone to thrombosis, as well as the left ventricular apex in patients with acute myocardial infarction or dilated cardiomyopathy. Infected vegetations or thrombi on the heart valves are also common sources of emboli. Undesirable material such as blood clots and infected vegetations can reside in the chambers of the right heart (atrium and ventricle), often associated with prosthetic material such as pacemaker leads or long-term indwelling catheters.

The most effective treatment for conditions resulting from the presence of blood clots or other undesirable materials within the circulation is, of course, to stabilize or eliminate the material before it has embolized. Alternatively, if obstruction to flow has already occurred but before the obstruction has caused permanent harm (infarction, shock, death), the material can be eliminated by utilizing biologic or mechanical means.

Biologic treatments involve the delivery of agents to the material, which either dissolve the material or, at a minimum, stabilize it until the body can eliminate it. In the case of infective vegetations, antimicrobial agents can, over time, decrease the chances of embolization. In the case of blood clots, the agents include 1) anticoagulant agents (heparin, warfarin, etc.) which prevent propagation of blood clots; and 2) more potent thrombolytic agents (streptokinase, urokinase, tPA, etc.,) which actively dissolve clots. The agents are usually delivered systemically, i.e., into a peripheral or central vein and allowed to circulate throughout the body. Thrombolytic agents can also be delivered through a catheter directly to the blood clot which can increase its effectiveness by increasing local concentrations but this does not completely eliminate the absorption into systemic circulation throughout the body.

Thrombolytic agents have been shown to increase survival in patients with hemodynamically significant pulmonary embolism as documented by echocardiographic evidence of right ventricular strain. The use of thrombolytic agents is the standard of care in this subgroup of patients with a high 20-25% early mortality. They are commonly used to dissolve clots in other blood vessels including arteries to heart, abdominal organs and extremities.

There are two primary disadvantages to thrombolytic agents. First, every cell in the body is exposed to the agent which can lead to serious and often life threatening bleeding complications in remote areas such as the brain and stomach. The risk of major bleeding complications can be as high as 25% and the risk of often fatal bleeding into the brain can go up to 3%. Second, blood clots undergo a process called organization where the soft gel-like red/purple clot is transformed into a firmer, whitish clot by the cross-linking of proteins such as fibrin. Organized clots are much less amenable to treatment with thrombolytic agents. Thromboemboli, such as pulmonary emboli, can contain a significant amount of organized clot since the thrombus frequently developed at its original site (e.g., the deep veins of the legs) over a long period of time prior to embolizing to the remote site (e.g., the lungs).

Mechanical treatments involve the direct manipulation of the material to eliminate the obstruction. This can involve aspiration, maceration, and compression against the vessel wall, or other types of manipulation. The distinct advantage of mechanical treatment is that it directly attacks the offending material and eliminates the vascular obstruction independent of the specific content of the offending material. Mechanical treatments, if feasible, can usually prove to be superior to biologic treatments for vascular obstruction. Procedural success rates tend to be higher. The best example of this advantage is in the treatment of acute myocardial infarction. Although thrombolytic therapy has had a major impact on the management of patients with myocardial infarction, this option is now relegated to a distant second choice. The clear standard of care today for an acute myocardial infarction is an emergency percutaneous coronary intervention during which the coronary artery obstruction is relieved by aspiration, maceration or balloon compression of the offending thrombus. This mechanical approach has been shown to decrease the amount of damaged heart tissue and improve survival relative to the thrombolytic biological approach.

Mechanical treatment, however, has played a limited role in the removal of blood clots found in larger blood vessels such as pulmonary arteries and heart chambers. Surgical pulmonary embolectomy involves opening the pulmonary artery and removing the offending clot under direct vision. This operation has been performed for nearly 100 years, but did not become practical until the introduction of the heart lung machine. Even then, it was generally relegated to a salvage procedure in moribund patients in whom all other options had been exhausted because of the inherent danger in the surgery and the recovery period. While surgical pulmonary embolectomy is very effective in completely evacuating pulmonary emboli whether soft-fresh and firm-organized clot, it is an invasive procedure.

Recent data has shown that the early outcomes with surgical pulmonary embolectomy are excellent, at least as good as thrombolytic treatment, as long as the procedure is performed in a timely fashion before the patient becomes very ill or suffers a cardiac arrest. The long term outcomes of patients surviving surgical pulmonary embolectomy have always been very good. Although these data have generated a renewed interest in performing surgical pulmonary embolectomy, its use remains limited because of the invasiveness of the procedure. Although minimally invasive approaches have been described, the standard procedure requires a 20-25 cm incision through the sternal bone and placing the patient on cardiopulmonary bypass (the heart-lung machine).

Catheter-based removal of blood clots from larger blood vessels (e.g., pulmonary arteries) and heart chambers has had limited success, at least compared to smaller blood vessels (e.g., coronary arteries). Catheter pulmonary embolectomy, where the pulmonary emboli are removed percutaneously using one of several techniques, has been around for nearly 30 years but few patients currently receive these therapies. These techniques can be subdivided into three categories. With fragmentation thrombectomy, the clot is broken into smaller pieces, most of which migrate further downstream, decreasing the central obstruction but resulting in a "no-reflow" phenomenon. It is sometimes used in combination with thrombolytics which preclude their use as an alternative to thrombolytics. With the rheolytic thrombectomy, high velocity saline jets create a Venturi effect and draw the fragments of the clot into the catheter. Finally, the aspiration techniques draw the clot into a catheter via suction. With a Greenfield embolectomy, the catheter with the attached clot is repeatedly drawn out of the vein. All of these techniques rely on catheters which are small compared to the size of the clots and blood vessels. Their limited success is likely related to their inability to achieve a complete en-bloc removal of the material without fragmentation.

The experience with catheter-based treatment of deep venous thrombus has also had limited success. The operator must use relatively small catheters to remove or break up large amounts of well embedded clot. This procedure is therefore time-consuming, inefficient and ultimately not very effective in removal of the whole clot.

It is clear that all of the therapeutic options available to patients with clot or other undesirable material in medium or large blood vessels, such as those with pulmonary embolism, have serious limitations. Anticoagulation only limits propagation of clot, it does not remove it. Thrombolytic therapy is not targeted, carries a real risk of major bleeding, and is not very effective in firm/organized clots. Catheter embolectomy uses technology developed for small blood vessels, does not scale well to material residing in medium and large vessels or heart chambers, and thus is not very effective. Surgical embolectomy is highly effective but highly invasive. There is a real need for a direct mechanical treatment that is as effective as surgical embolectomy but can be performed using endovascular techniques.

Current efforts to apply existing catheter embolectomy technologies to medium to large blood vessels and heart chambers encounter at least two obstacles: fragmentation and excessive blood loss. Techniques which depend on fragmentation of the material tend to be inefficient and ineffective in medium to large blood vessels and heart chambers because the flow of blood will carry a significant portion of the fragmented material away before it can be captured in the catheter. On the other hand, techniques which depend on aspiration of undesirable material will result in excessive blood loss as the size of the catheter increases.

A need therefore exists for a system and method to endovascularly remove undesirable material residing in medium to large blood vessels and heart chambers with minimal fragmentation and without excessive blood loss.

SUMMARY OF THE INVENTION

The present invention relates generally to systems and methods for removing undesirable material residing in vessels, such as blood vessels, or within chambers of the heart. More specifically, the subject invention relates to systems and methods for using a cannula to remove substantially en bloc, from a site of obstruction or interest, an undesirable material, such as blood clots, embolisms and thromboembolisms, without significant fragmentation and without excessive fluid loss. In addition, the systems and methods of the present invention may simultaneously reinfuse aspirated (i.e., removed) and filtered fluid, such as blood, back into the patient on a substantially continuous basis to minimize any occurrences of fluid loss and/or shock. The subject invention may be particularly useful, but may not be limited to, the removal of blood clots, tumors, infective vegetations and foreign bodies from medium to large blood vessels and heart chambers.

In one embodiment, a system is provided which includes a cannula and a secondary device. The cannula includes an expandable member, a cannula lumen, and a cannula proximal end. The expandable member includes a proximal most end, a distal most end, at least two moveable sections, with a space between the at least two moveable sections, and an impermeable membrane extending across the space between each of the at least two moveable sections and extending from the expandable member distal most end to the expandable member proximal most end. The secondary device is configured to be coaxially placed through the cannula lumen. The cannula proximal end is configured to operatively couple to a vacuum source configured to create a negative pressure to pull an undesirable material into the cannula lumen.

In another embodiment, a system is provided which includes a cannula and a macerator. The cannula includes a cannula lumen, cannula proximal end, a cannula distal end, and an expandable funnel coupled to the cannula distal end. The expandable funnel is defined by multiple moveable members, with a space between each of the multiple moveable members, and an impermeable membrane extending across the space between each of the multiple moveable members and extending from a distal most end of the expandable funnel to a proximal most end of the expandable funnel. The cannula proximal end is configured to operatively couple to a vacuum source configured to create a negative pressure to pull an undesirable material into the cannula lumen. The macerator is configured to be coaxially placed through the cannula lumen, where the macerator is configured to macerate the undesirable material and aid in the removal of the undesirable material.

In a further embodiment, a system is provided which includes a cannula and a fragmentation thrombectomy device. The cannula includes a cannula lumen, a cannula proximal end, a cannula distal end, a radiopaque member configured to aid in visualization of the cannula, and an expandable funnel coupled to the cannula distal end. The expandable funnel is defined by an actuating unit including a plurality of actuating members and an impermeable membrane. The impermeable membrane extends across a space between each of the adjacent actuating members of the plurality of actuating members and surrounds an entirety of the actuating unit. The cannula proximal end is configured to operatively couple to a vacuum source configured to create a negative pressure to pull an undesirable material into the cannula lumen. The fragmentation thrombectomy device is configured to be coaxially placed through the cannula lumen, where the fragmentation thrombectomy device is configured to disrupt or dislodge the undesirable material and aid in the removal of the undesirable material.

In another embodiment, a system for removing an undesirable material from within a vessel is provided. The system includes a first cannula having a distal end and an opposing proximal end. The distal end of the first cannula, in an embodiment, may include or may be deployable to a diameter relatively larger than that of the proximal end. The first cannula may be designed for maneuvering within the vessel to a site of interest, such that an undesirable material can be captured substantially en bloc through the distal end and removed along the first cannula away from the site. The system may also include a pump, in fluid communication with the proximal end of the first cannula, so as to provide a sufficient suction force for removing the undesirable material from the site of interest. The system may further include a second cannula in fluid communication with the pump, so that fluid removed from the site of interest by the first cannula can be directed along the second cannula and reinfused through a distal end of the second cannula. In one embodiment, the distal end of the second cannula may be situated in spaced relation to the distal end of the first cannula. The system may also be provided with a filter device positioned in fluid communication with the first cannula. The filter device, in an embodiment, may act to entrap or capture the undesirable material and remove it from the fluid flow. The system may further be provided with a reservoir in fluid communication with the filter device. The reservoir may act to transiently collect fluid being directed from the filter device and to provide a source of fluid for reinfusion by the second cannula. A second filter may also be included in fluid communication between the pump and the second cannula, so as to remove, prior to reinfusion, any debris that may have escaped from the filter device from the fluid flow.

In another embodiment, there is provided a method for removing an undesirable material from within a vessel. The method includes initially maneuvering a first cannula having a distal end and an opposing proximal end to a site of interest within the vessel, such that the distal end of the first cannula is positioned adjacent to the undesirable material. Next, a second cannula, in fluid communication with the first cannula, may be positioned such that its distal end can be situated in spaced relation to the distal end of the first cannula. Thereafter, a suction force may be provided through the distal end of the first cannula to the site of interest, so as to remove, through the distal end of the first cannula, the undesirable material substantially en bloc from the site of interest. Subsequently, any fluid removed along with the undesirable material may be reinfused, through the distal end of the second cannula, to a location in spaced relation from the distal end of the first cannula. The suction and reinfusion of blood can occur, in an embodiment, continuously for a desired duration to minimize fluid loss in the patient. Alternatively, the step of suctioning an undesirable material can occur at an intermittent pulse for a desired duration following reinfusion of the removed fluid.

In a further embodiment, an apparatus for removing an undesirable material from within a vessel is provided. The apparatus includes an elongated tube having a distal end through which an undesirable material can be captured, a pathway extending along the tube to provide a passage for transporting the undesirable material from the distal end, and a proximal end in opposing relations to the distal end through which the undesirable material can exit. The apparatus also includes a funnel situated at the distal end of the tube, and designed for deployment between a flared open position and a collapsed closed position, so as to better engage and capture the undesirable material. The apparatus further includes a mechanism positioned about a distal portion of the tube, which mechanism, upon actuation, can deploy the funnel between the closed position and the open position. In one embodiment, the funnel includes a plurality of strips, with each strip being pivotally coupled at one end to the distal end of the tube. The funnel may also include a substantially impermeable membrane extending across a space between adjacent strips, such that the membrane, in connection with the strips define the shape of the funnel. The mechanism, in an embodiment, includes a balloon positioned circumferentially about the tube at a location proximal to the funnel, and an attachment mechanism provided with one end attached to the funnel and an opposite end attached to the balloon. By design, upon expansion of the balloon, the attachment mechanism can pull on the funnel to deploy it into a flared open position. The apparatus may also include a jacket positioned circumferentially about the distal end of the tube, and extending from the funnel to the balloon to protect the vessel from potential irritation that may be caused by the balloon and the strips defining the funnel. As the jacket may be attached to the funnel and the balloon, in one embodiment, the jacket may act as the mechanism for deploying the funnel into a flared open position upon expansion of the balloon.

BRIEF DESCRIPTION OF THE DRAWINGS

These and other features and advantages of the present invention will become more apparent from the following detailed descriptions taken in conjunction with the accompanying drawings wherein like reference characters denote corresponding parts throughout the several views.

DETAILED DESCRIPTION OF SPECIFIC EMBODIMENTS

As noted above, existing catheter techniques may not be effective in removing undesirable material, such as clots, from medium and large size blood vessels or from heart chambers, because these catheters tend to be small relative to the material to be removed. As a result, the material often needs to be fragmented in order to fit within the catheter. However, with fragmentation, the chances of the fragments being carried away in the bloodstream increases, resulting in downstream obstruction. If the catheter is enlarged to accommodate the larger structure and material, such a catheter may aspirate an unacceptable volume of blood, resulting in excessive fluid loss and/or shock in the patient.

The present invention overcomes the deficiencies of existing devices and techniques and can act to remove substantially en bloc (i.e., wholly or entirely) undesirable material, such as thrombi and emboli, from the vasculature, including medium to large size blood vessels, and from heart chambers. Vessels from which the undesirable material may be removed, in accordance with an embodiment of the present invention, include, for example, those within the pulmonary circulation (e.g., pulmonary arteries), systemic venous circulation (e.g., vena cavae, pelvic veins, leg veins, neck and arm veins) or arterial circulation (e.g., aorta or its large and medium branches). The heart chambers may be, for example, in the left heart (e.g., the left ventricular apex and left atrial appendage), right heart (e.g., right atrium and right ventricle), or on its valves. The present invention can also act to remove tumors, infective vegetations and other foreign bodies.

Although reference is made to medium and large vessels, it should be appreciated that the systems and methods, hereinafter disclosed, can be scaled and adapted for use within smaller vessels within the body, if desired.

Figure 1:
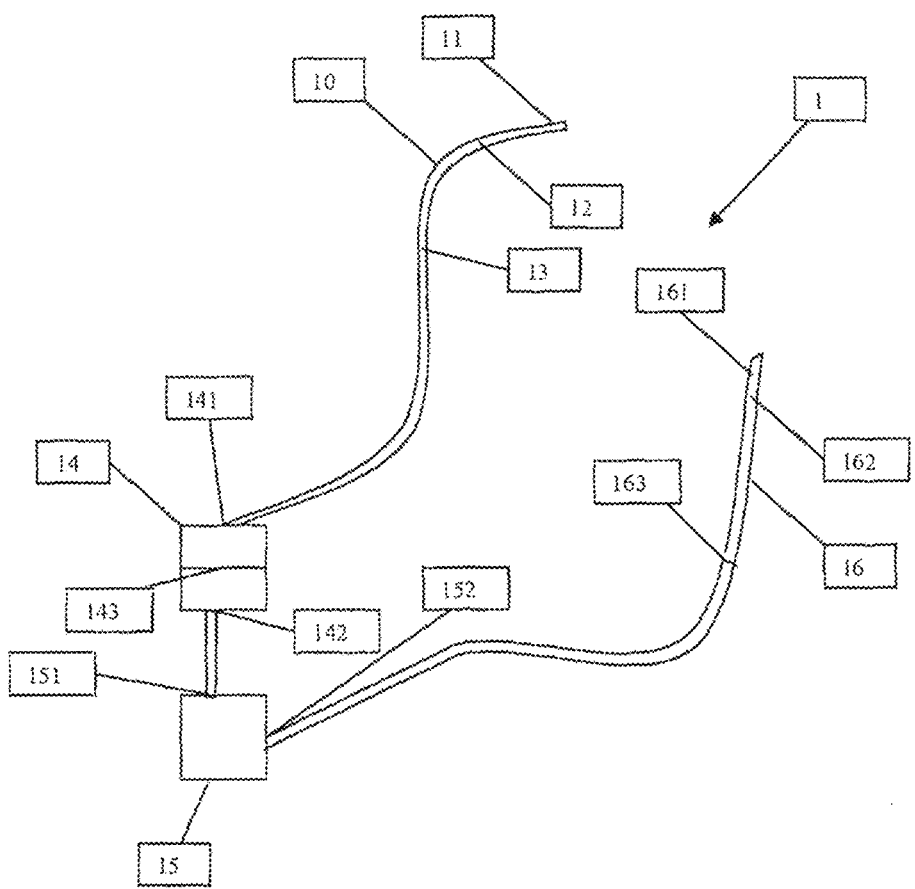
FIG. 1 illustrates system for removing an undesirable material from within a vessel in accordance with one embodiment of the present invention.

Referring now to FIG. 1, there is illustrated a system 1 for removing an undesirable material, substantially en bloc, from an obstruction site or site of interest within the vasculature, and for reinfusion of fluid removed (i.e., suctioned or aspirated) from the site of interest back into a patient, in order to minimize fluid loss within the patient. System 1, in an embodiment, may be provided with a first or suction cannula 10 for capturing and removing en bloc the undesirable material from the site of interest, such as that within a blood vessel or a heart chamber. Cannula 10, in an embodiment, may be an elongated tube and may include a distal end 11 through which the undesirable material can be captured and removed. Cannula 10 may also include a lumen or pathway 12 extending along a body portion of cannula 10. Pathway 12, in one embodiment, provides a passage along which the captured material and aspirated circulatory fluid, such as blood, that may be captured therewith may be transported and directed away from the site of interest. Cannula 10 may further include a proximal end 13 in opposing relations to the distal end 11, and through which the captured material may exit from the cannula 10.

Since cannula 10 may be designed for introduction into the vasculature, for instance, through a peripheral blood vessel, and may need to subsequently be maneuvered therealong to the site of interest, cannula 10, in an embodiment, may be made from a pliable material. In addition, as cannula 10 may be used to introduce a suction force to the site of interest for capturing the undesirable material, cannula 10 may be made from a sufficiently stiff material or may be reinforced with a sufficiently stiff material, so as not to collapse under a suction force. In one embodiment, cannula 10 may be constructed from a biocompatible material, such as polyvinyl chloride, polyethylene, polypropylene, polyurethane, polyether block amide (Pebax®), silicone, or a combination thereof.

In certain instances, it may be desirable to maneuver cannula 10 to the site of interest using image guidance, for example, using fluoroscopy or echocardiography. In order to permit cannula 10 to be visualized, cannula 10, in an embodiment, may also include a radiopaque material or any material capable of being visualized.

Figures 2A, 2B, 2C:
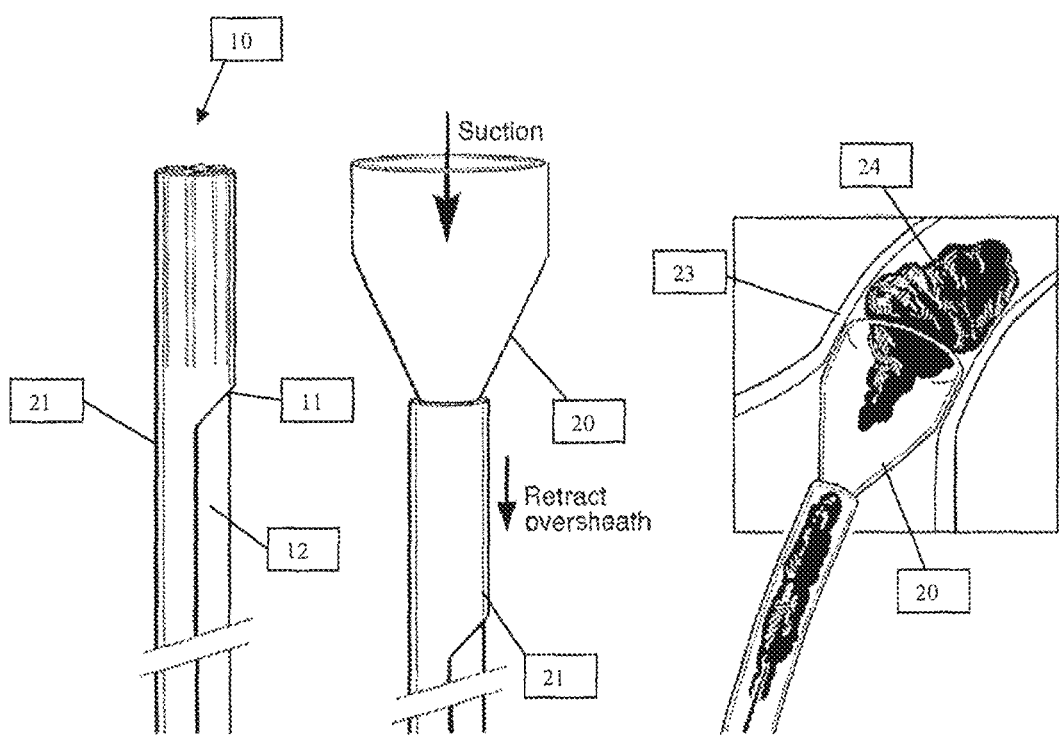
FIGS. 2A-H illustrate a distal end of a suction cannula in operation in connection with the system shown in FIG. 1.
Figure 2D:
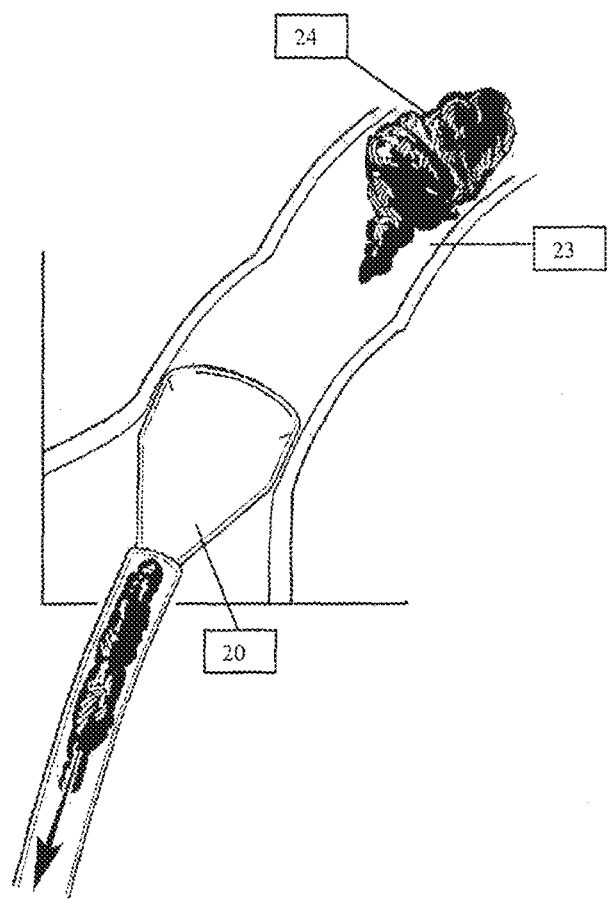

To better engage and capture the undesirable material substantially en bloc and without significant fragmentation, the distal end 11 of cannula 10 may be designed to have a diameter that can be relatively larger than that of the proximal end 13. In one embodiment, as illustrated in FIGS. 2A-D, distal end 11 of cannula 10 may be in the shape of a funnel 20, and may be provided with a diameter, for example, approximately at least three times that of pathway 12. Of course, depending on the surgical procedure being implemented, the ratio between the diameter of funnel 20 and pathway 12 can be varied, if so desired. Funnel 20, with its design, may be placed directly at a site of interest 23 to engage undesirable material 24 (FIG. 2C), or spatially away from the site of interest 23 to capture the undesirable material 24 (FIG. 2D). In a situation where the distal end 11 may be situated spatially away from the site of interest, by providing distal end 11 with funnel 20, a vortex effect may be generated during suctioning to better direct the undesirable material into the funnel 20. It is believed that fluid flowing into funnel 20 can often exhibit a laminar flow circumferentially along the interior surface of the funnel 20 to generate a vortex flow into the distal end 11 of suction cannula 10. Thus, in the presence of a vortex flow, such a flow can act to direct the undesirable material toward the distal end 11 to allow the material to subsequently be pulled into the distal end by suctioning.

To provide a funnel shaped distal end, cannula 10 may include, in an embodiment, a sheath 21 circumferentially situated about distal end 11 of cannula 10. Sheath 21, as illustrated, may be designed to slide toward as well as away from the distal end 11 of cannula 10. In that way, when the distal end 11 is positioned at the site of interest 23, and sheath 21 is retracted (i.e., slid away from the distal end 11), funnel 20 may be exposed and expanded into the desired shape in order to engage undesirable material 24. To collapse funnel 20, sheath 21 may be advanced toward the distal end 11 and over the funnel 20. Thereafter, cannula 10 may be maneuvered from the site of interest 23.

Figures 2E, 2F, 2G:
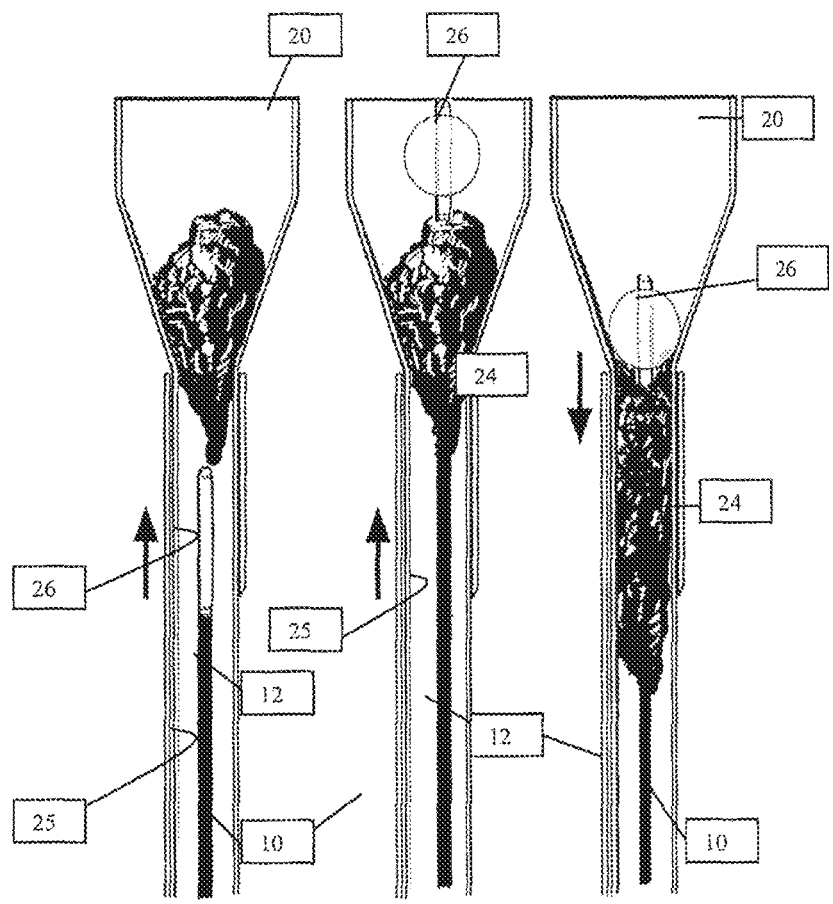
Figure 2H:
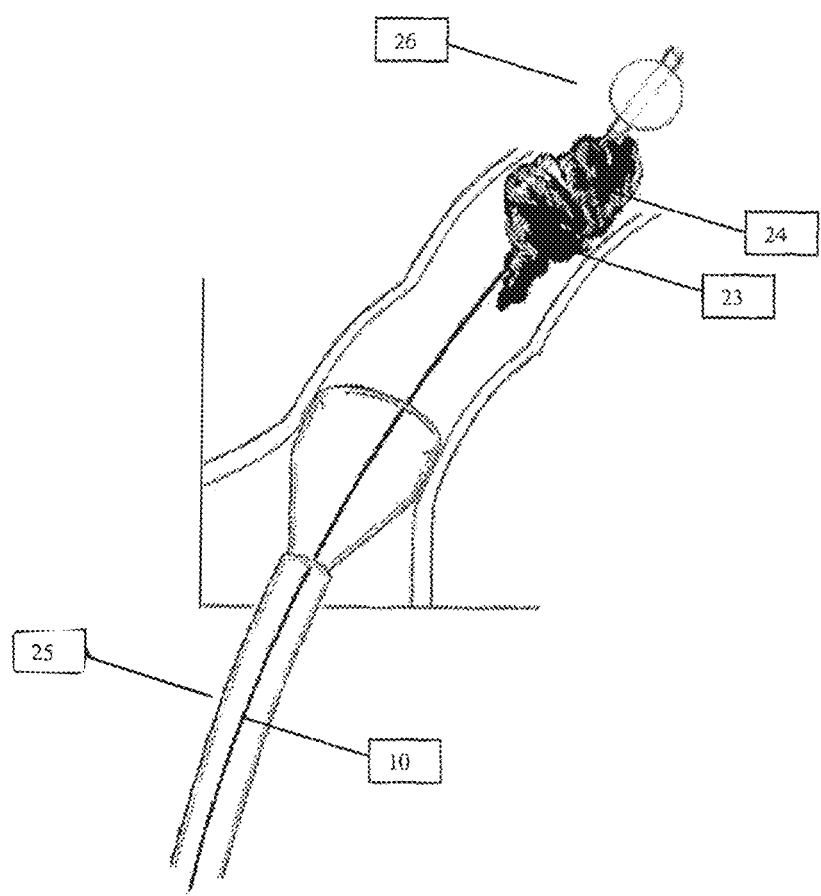

In order to enhance capture and removal of the undesirable material 24, looking now at FIGS. 2E-G, cannula 10 may be designed to allow introduction of a catheter 25 with balloon 26 to the site of interest. In an example where the undesirable material 24 may be entrapped within funnel 20, catheter 25 with balloon 26 may be directed along the lumen or pathway 12 of cannula 10 and into funnel 20. Once catheter 25 has been advanced past the undesirable material 24 within funnel 20, balloon 26 may be inflated to a size sufficient to pull on the undesirable material entrapped within funnel 20. As balloon 26 is pulled down the funnel 20 towards pathway 12, balloon 26 can dislodge the entrapped material and can eventually partially or substantially occlude a pathway 12, distal to the undesirable material 24, which in essence occludes the fluid communication between cannula 10 and the vessel. The suction force within pathway 12, as a result, can be enhanced to better remove the undesirable material. Similarly, as shown in FIG. 2H, in a situation where undesirable material 24 may be firmly lodged in the vessel at the site of interest 23 and the suction applied by cannula 10, spatially situated away from the site of interest 23, may be insufficient to dislodge the undesirable material 24, catheter 25 and balloon 26 may be advanced past the distal end of cannula 10 and past the undesirable material 24 at the site of interest 23. Once past the undesirable material 24 the balloon 26 may be inflated and as balloon is withdrawn back towards the distal end 11 of cannula 10, it can dislodge the undesirable material and allow the suction to draw it into the distal end of cannula 10. Of course, this approach can also be applied when cannula 10 is situated directly at the site of interest 23 and the suction force may be insufficient to dislodge the undesirable material 24.

Figure 3A:
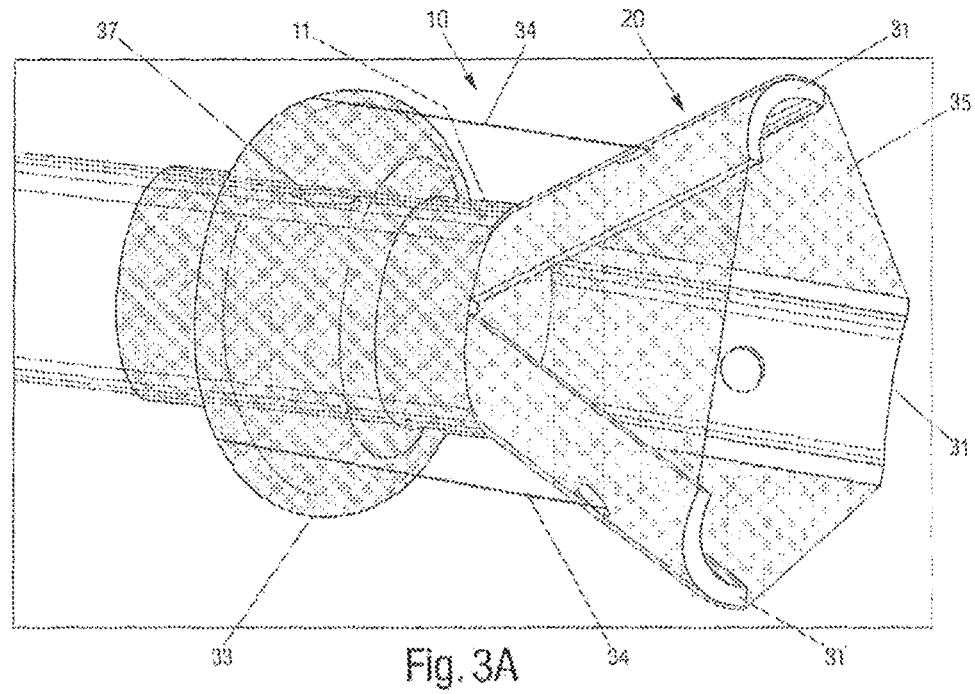
FIGS. 3A-B illustrate an alternate distal end of a suction cannula used in connection with the system shown in FIG. 1.
Figure 3B:
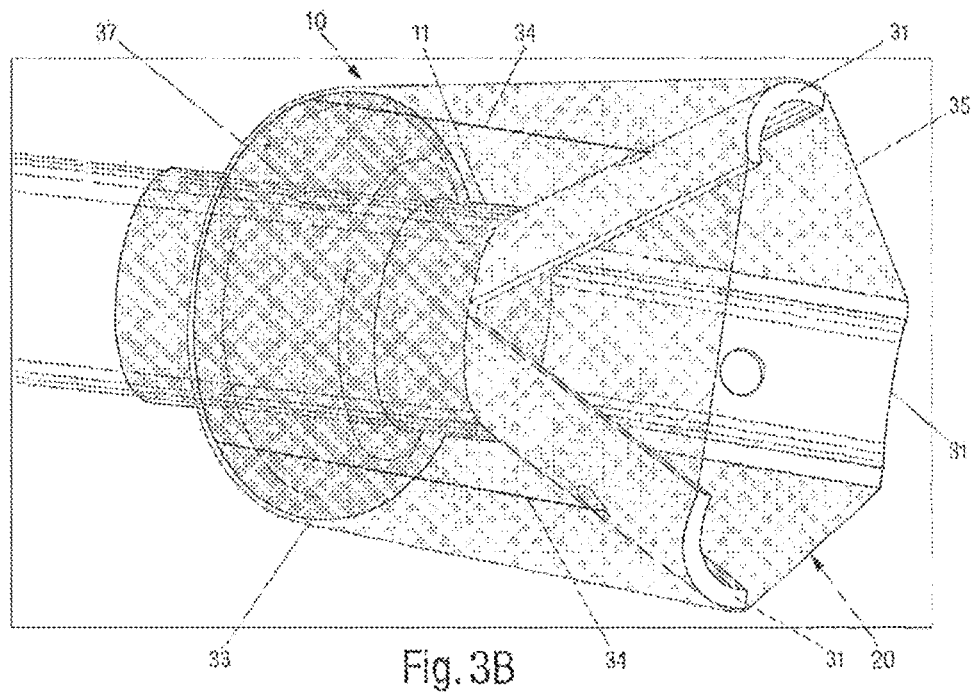

In another embodiment, looking now at FIG. 3A-B, funnel 20 located at distal end 11 of cannula 10 may be created by providing a plurality of independent strips 31, each coupled at one end to distal end 11 of cannula 10. In the embodiment shown in FIG. 3A, three strips 31 are illustrated. However, it should be appreciated that two or more strips 31 may be used, if so desired. Strips 31, in an embodiment, may be designed to pivot between a closed position, where strips 31 may be substantially adjacent one another, and an open position, where strips may be flared into a funnel 20, shown in FIG. 3A. To deploy strips 31, and thus funnel 20, between an open and closed position, cannula 10 may include a balloon 33 positioned circumferentially about cannula 10 and proximal to strips 31. In addition, an attachment mechanism, such as a string 34 or any similar mechanisms (e.g., rod, chain etc.), may be provided for each of the strips 31, with one end attached to one strip 31 and an opposite end attached to balloon 33. In this way, when balloon 33 is inflated and expands radially, balloon 33 may pull on each attachment mechanism 34, so as to deploy strips 31 into a flared open position. Balloon 33, in one embodiment, may be inflated through opening 37 through the use of any fluid, including water, air, or radiopaque contrast material. It should be noted that securing of the attachment mechanism to the strips 31 and balloon 33 can be accomplished using any methods or mechanisms known in the art. For instance, adhesives, knots, or soldering etc. may be used. Moreover, to the extent desired, strips 33 and balloon 31 may be designed to expand to a diameter larger than that of the vessel within which cannula 10 is being deployed. In that way, cannula 10 may be securely positioned at the site of interest for removal of the undesirable material substantially en bloc.

To better capture the undesirable material and direct it into the canals 10, a membrane 35 may be placed across a space between adjacent strips 31 when the strips 31 are in the open position. In one embodiment, a continuous membrane 35 may be used to circumferentially stretch across each of the spaces between adjacent strips 31. Membrane 35 may also act to enhance suction at the site of interest, as it can cover up any open space between the strips 31. To that end, membrane 35, in an embodiment, may be made from a non-permeable material. It should be appreciated that membrane 35 and strips 31, as illustrated, together define funnel 20 at distal end 11 of cannula 10.

Furthermore, to protect the vessel from irritation or damage that may be caused by the presence of balloon 33 and/or strips 31, jacket 36, as shown in FIG. 3B, may be provided circumferentially about the distal 11 of cannula 10. In an embodiment, jacket 36 may extend substantially from a tip of each strip 31 to balloon 33. Jacket 36, however, can be affixed anywhere along each strip 31, if necessary. Since jacket 36 attaches at one end to strips 31 and at an opposite end to balloon 33, jacket 36, in an embodiment, may be used instead of attachment mechanism 34 to deploy strips 31 into an open position when balloon 33 is expanded. Of course, jacket 36 may also be used in conjunction with attachment mechanism 34 to deploy strips 31 into an open position. Furthermore, in one embodiment, jacket 36 may be lengthened, so that the end connected to strips 31 may instead be pulled over strips 31, into funnel 20, and attached substantially to a base of each strips 31 (i.e., base of funnel 20). With such a design, membrane 35 may not be necessary, as jacket 36 may serve the purpose of membrane 35 to cover the space between each of strips 31. In such an embodiment, at least that portion of jacket 36 extending over strips 31 and into the base funnel 20 can be impermeable.

In certain instances, balloon 33 may act to enhance the suction force being applied at the site of interest when removing the undesirable material. For instance, when cannula 10 is deployed downstream of the undesirable material, rather than substantially adjacent to the undesirable material, within a vessel having a venous circulation (i.e., flow toward the heart), balloon 33, when expanded radially, can substantially occlude the vessel, such that collateral fluid flow within the vessel can be minimized, thereby increasing the suction force that can be applied to the undesirable material. Additionally, the occlusion of such a vessel by balloon 33 can better direct the material being removed into the funnel 20 and prevent the material from being carried by the flow of blood past the funnel.

Alternatively, when cannula 10 is deployed upstream of the undesirable material within a vessel having an arterial circulation (i.e., flow away from the heart), rather than substantially adjacent to the undesirable material, balloon 33, when expanded radially, can substantially occlude the vessel, such that pressure being exerted on the downstream material by the fluid flow can be lessened. By lessening the pressure on the material to be removed, the suction force being applied at the site of interest can act to remove the material more easily.

Figure 4A:
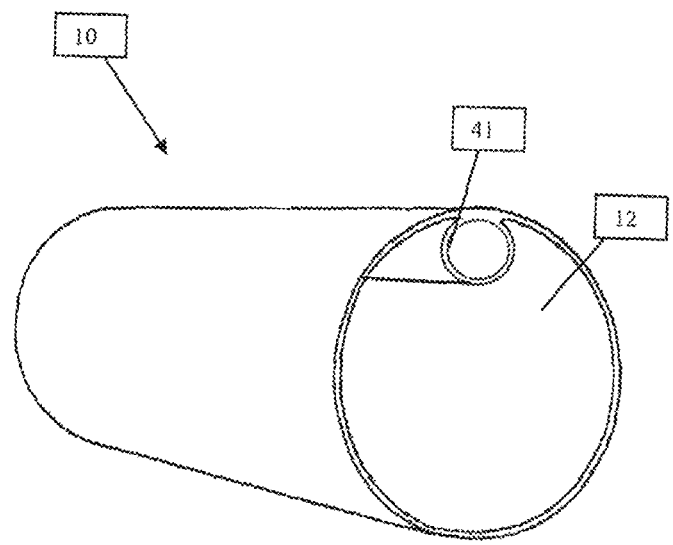
FIG. 4A-E illustrate a variety of cannulas for use in connection with the system shown in FIG. 1.

As suction cannula 10 may be made from a pliable material, in order to efficiently direct it along a vessel to the site of interest, cannula 10 may be reinforced with wire or other material to optimize maneuverability within the vessel without kinking. Referring now to FIG. 4A, suction cannula 10 may, in addition to pathway 12, be provided with one or more additional pathway or lumen 41. In this multi-lumen design, pathway 12 may act, as noted above, to provide a passage along which the captured material may be transported and directed away from the site of interest. Lumen 41, on the other hand, can provide a passage along which a fluid can be directed to inflate balloon 33 through opening 37 (FIGS. 3A-B). In certain embodiments, lumen 41 may also be used to accommodate other devices, such as other catheters or surgical instruments, for use in connection with a variety of purposes. For example, a device may be inserted and advanced along lumen 41 through the distal end 11 of suction cannula 10 to dislodge the undesirable material. An angiography catheter can be inserted and advanced along lumen 41 through the distal end 11 of suction cannula 10 to perform an angiogram to confirm the location of the undesirable material or confirm that it has been successfully removed. A balloon embolectomy catheter can be inserted along lumen 41 toward the distal end 11 of suction cannula 10 to remove any material which may have clogged the cannula or past the any undesirable material firmly lodged in the vessel to draw it into the cannula. Although illustrated with such a multi-lumen design, any other multi-lumen design may be possible.

Figure 5:
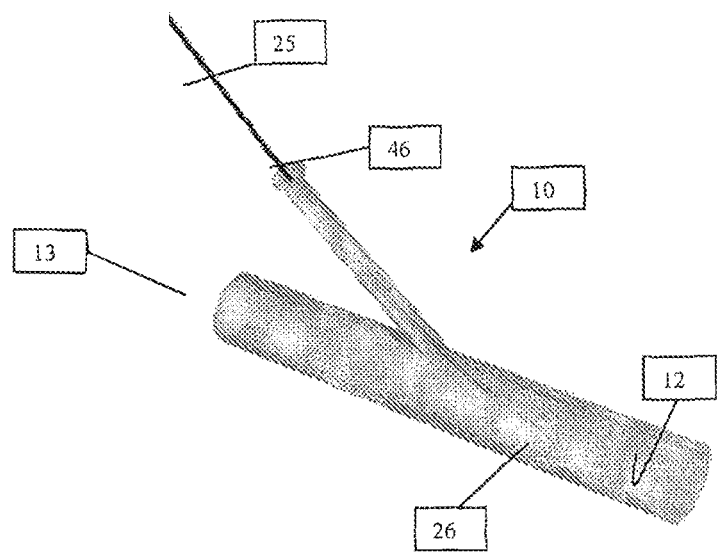
FIG. 5 illustrates a port through which another device may be introduced within a suction cannula used in connection with the system shown in FIG. 1.

To introduce other devices, such as catheter 25 with balloon 26, into lumen 41 or pathway 12, cannula 10 may be provided with a port 51, as shown in FIG. 5, located at the proximal end 13 of cannula 10. It should be appreciated that in the embodiment where cannula 10 has only pathway 12 (i.e., single lumen cannula), port 51 may similarly be provided at the proximal end 13 of cannula 10 to allow the introduction of other devices into pathway 12.

Cannula 10 of the present invention may be of any sufficient size, so long as it can be accommodated within a predetermined vessel, such as a medium to large size blood vessel. The size of cannula 10 may also be determined by the size of the undesirable material to be removed, so long as the undesirable material can be removed substantially en bloc without significant fragmentation. In one embodiment, suction cannula 10 may be designed to remove at least 10 cm3 of undesirable material substantially en bloc. Of course, cannula 10 can be scaled and adapted for use within smaller vessels in the body and for removing a relatively smaller volume or amount undesirable material, if so desired.

Looking again at FIG. 1, system 1 can also include filter device 14 in fluid communication with the proximal end 13 of cannula 10. Filter device 14, in one embodiment, may include an inlet 141 through which fluid removed from the site of interest along with the captured undesirable material can be directed from cannula 10. Filter device 14 may also include an outlet 142 through which filtered fluid from within device 14 may be directed downstream of system 1. To prevent the undesirable material captured from the site of interest from moving downstream of system 1, filter device 14 may further include a permeable sheet 143 positioned within the fluid flow between the inlet 141 and the outlet 142.

Permeable sheet 143, in an embodiment, may include a plurality of pores sufficiently sized, so as to permit fluid from the site of interest to flow therethrough, while preventing any undesirable material captured from the site of interest from moving downstream of system 1. Examples of permeable sheet 143 includes coarse netting, fine netting, a screen, a porous filter, a combination thereof or any other suitable filter material capable of permitting fluid to flow through while impeding movement of the captured undesirable material. It should be noted that, rather than just one, a plurality of permeable sheets 143 may be used. Alternatively, one permeable sheet 143 may be folded to provide multiple surfaces, similar to an accordion, for use in connection with filter device 14. By using a plurality of permeable sheets 143 or by folding sheet 143, the number of filtration surfaces through which the fluid must flow increases to enhance filtration and further minimize any occurrence of any undesirable material from moving downstream of system 1.

Although a permeable sheet 143 is described, it should be appreciated that filter device 14 may be provided with any design capable of entrapping the undesirable material, while allowing fluid to move therethrough. To that end, filter device 14 may include a mechanical trap to remove the undesirable material from the fluid flow. Such a mechanical trap may be any trap known in the art and may be used with or without permeable sheet 143.

Still looking at FIG. 1, system 1 may also be provided with a pump 15 designed to generate negative pressure, so as to create a necessary suction force through cannula 10 to pull any undesirable material from the site of interest. In one embodiment, pump 15 may include an intake port 151 in fluid communication with outlet 142 of filter device 14. Intake port 151, as illustrated, may be designed to receive filtered fluid from filter device 14. Pump 15 may also be designed to generate the positive pressure, so as to create a necessary driving force to direct fluid through exit port 152 and downstream of system 1 for reinfusion of fluid removed from the site of interest back into the body. In an embodiment, the suction force and the drive force may be generated by pump 15 simultaneously and may take place continuously or intermittently for a set duration. Pump 15, as it should be appreciated, may be any commercially available pump, including those for medical applications and those capable of pumping fluids, such as blood. Examples of such a pump includes a kinetic pump, such as a centrifugal pump, and an active displacement pump, such as a rollerhead pump.

In an alternate embodiment, an independent vacuum device (not shown), may be provided for generating the necessary suction force at the site of interest, while a pump 15 may act to generate the necessary driving force for reinfusion purposes. In such an embodiment, pump 15 may be in fluid communication with the filter device 14, while the vacuum device may be in fluid communication with suction cannula 10 upstream to the filter device 14. The independent pump 15 and vacuum device may operate intermittently for a set duration, and if desired, either the vacuum device or pump 15 may operate continuously, while the other operates intermittently.

Downstream of pump 15, system 1 may further include a second or reinfusion cannula 16 in fluid communication with the exit port 152 of pump 15. Reinfusion cannula 16, in an embodiment, may be designed to permit filtered fluid, directed from filter device 14 by way of pump 15, to be reinfused back into a patient at a desired site. To that end, reinfusion cannula 16 may be designed for placement within the same or different vessel within which suction cannula 10 may be located.

Reinfusion cannula 16, in one embodiment, may be an elongated tube and includes a distal end 161 through which cleansed or filtered fluid can be reinfused back into the body. In an embodiment, distal end 161 of reinfusion cannula 16 may be designed so that it can be situated in spaced relation to the distal end 11 of the suction cannula 10 when system 1 is in operation. Reinfusion cannula 16 may also include a lumen or pathway 162 extending along its body portion to provide a passage along which the filtered fluid, such as blood, may be transported to a reinfusion site. Reinfusion cannula 16 may further include a proximal end 163 in opposing relations to the distal end 161, and through which the filtered fluid from pump 15 may enter into the cannula 16.

Furthermore, similar to suction cannula 10, since reinfusion cannula 16 may be designed for introduction into the vasculature, and may need to be maneuvered therealong, reinfusion cannula 16, in one embodiment, may be made from a pliable material. In one embodiment, reinfusion cannula 16 may be constructed from a biocompatible material, such as polyvinyl chloride, polyethylene, polypropylene, polyurethane, polyether block amide (Pebax®), silicone, or a combination thereof. In certain instances, it may be desirable to maneuver reinfusion cannula 16 to the reinfusion site using image guidance, for example, using fluoroscopy or echocardiography. To permit reinfusion cannula 16 to be visualized, reinfusion cannula 16, in an embodiment, may also be made to include a radiopaque material.

Figure 4B:
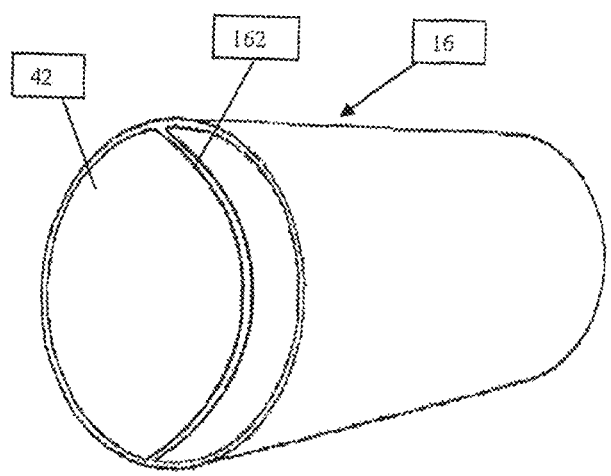

Since reinfusion cannula 16 may be made from a pliable material, in order to efficiently direct it along a vessel to the reinfusion site, reinfusion cannula 16 may be reinforced to optimize maneuverability within the vessel without kinking. Moreover, as shown in FIG. 4B, reinfusion cannula 16 may be provided with one or more additional lumens. With a multi-lumen design, lumen 162, as noted above, may act to provide a passage along which the filtered fluid may be transported and directed to the reinfusion site. Lumen 42, on the other hand, can provide a passage through which a guide wire can be inserted to assist in the guiding the reinfusion cannula 16 to the reinfusion site, or through which other instruments and devices may be inserted for various surgical procedures. With such a multi-lumen design, reinfusion cannula 16 can serve as an introducer sheath by providing lumen 42 through which these instruments can pass, while filtered blood can be reinfused through lumen 162. Although illustrated with such a multi-lumen design, any other multi-lumen design may be possible.

Figure 4C:
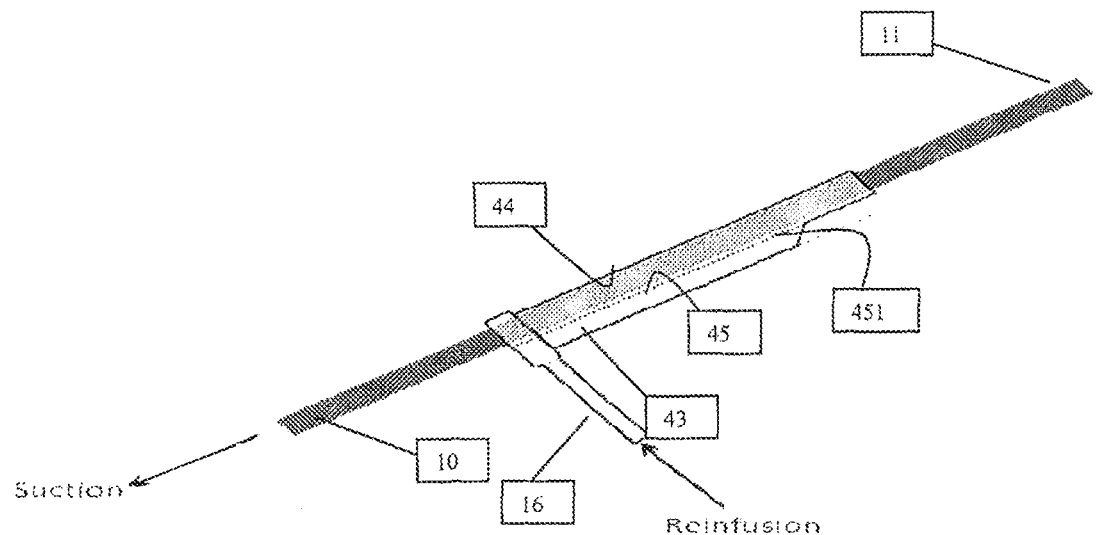

Although illustrated as a separate component from suction cannula 10, in certain embodiments, the reinfusion cannula 16 may be designed to be substantially integral with suction cannula 10. In one embodiment, as illustrated in FIG. 4C, reinfusion cannula 16 may be incorporated as part of a double or multi-lumen introducer sheath 43 for insertion into the same vessel within which the suction cannula 10 may be situated. In particular, suction cannula 10 may be inserted and maneuvered through one lumen 44 of sheath 43, while reinfusion cannula 16 may be in fluid communication with lumen 45 of sheath 43. In such an embodiment, lumen 45 may include a distal end 451 in spaced relations to the distal end 11 of cannula 10, so that cleansed or filtered fluid may be introduced to the reinfusion site away from the site of interest where the distal end 11 of cannula 10 may be positioned.

Figure 4D:
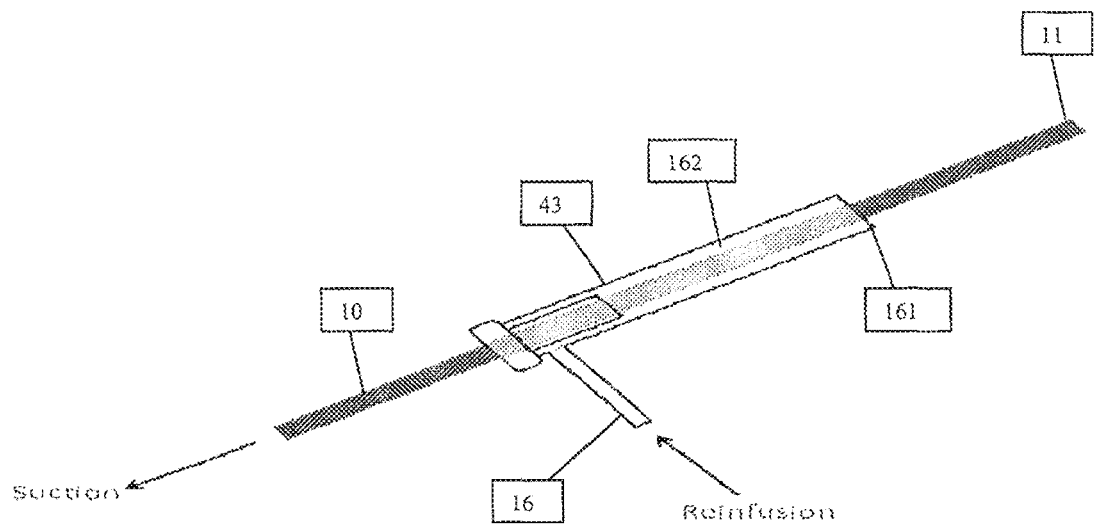

Alternatively, as illustrated in FIG. 4D, reinfusion cannula 16 may be incorporated as part of a double or multi-lumen introducer sheath 43 where the reinfusion cannula 16 and the suction cannula 10 may be concentrically aligned along a shared axis A. In the embodiment shown in FIG. 4D, reinfusion cannula 16 may have a diameter that can be relatively larger than that of suction cannula 10. To that end, reinfusion cannula 16 can accommodate suction cannula 10 within pathway 162 of the reinfusion cannula 16, and allow suction cannula 10 to extend from within pathway 162, such that the distal end 11 of suction cannula 10 may be positioned in spaced relations relative to the distal end 161 of reinfusion cannula 16. The spaced relations between distal end 161 and distal end 11 allows filtered fluid to be introduced to the reinfusion site away from the site of interest, where the removal of the undesirable material may be occurring.

Figure 4E:
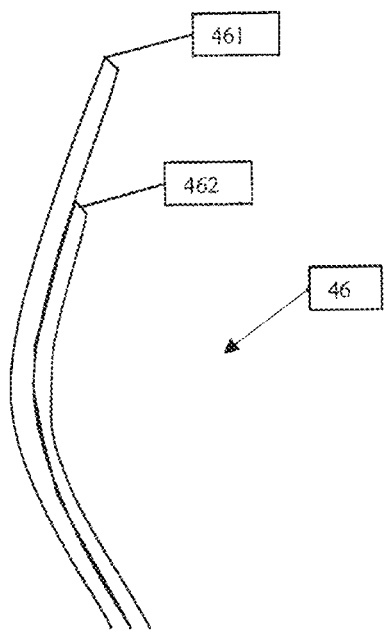

In another embodiment, reinfusion cannula 16 and suction cannula 10 can be integrated into a single multi-lumen suction-reinfusion cannula 46, as shown in FIG. 4E. In the embodiment shown in FIG. 4E, multi-lumen cannula 46 may include a distal suction port 461 through which undesirable material from the site of interest can be removed, and a proximal reinfusion port 462 through which cleansed or filtered fluid may be reinfused back into the body. The spaced relations between the suction port 461 and reinfusion port 462 allows filtered fluid to be introduced to the reinfusion site away from the site of interest where the removal of the undesirable material may be occurring.

In an embodiment, the size of the reinfusion cannula, whether independent from the suction cannula, part of a multi-lumen introducer sheath, part of a multi-lumen combined suction-reinfusion cannula, or in concentric alignment with the suction cannula, may be designed so that it can handle a relatively rapid reinfusion of large volumes of fluid by pump 15.

Figure 6:
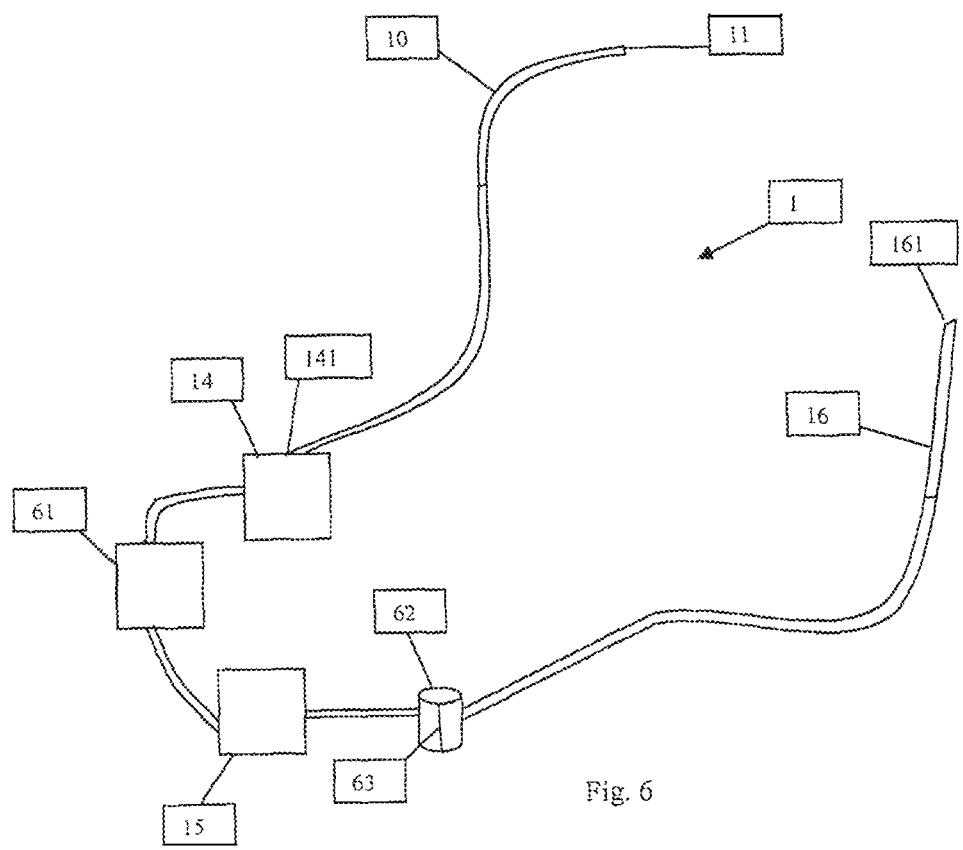
FIG. 6 illustrates a system for removing an undesirable material from within a vessel in accordance with another embodiment of the present invention.

With reference now to FIG. 6, system 1 may also include a reservoir 61. Reservoir 61, in one embodiment, may be situated in fluid communication between filter device 14 and pump 15, and may act to transiently collect fluid filtered from the site of interest, prior to the filtered fluid being directed into reinfusion cannula 16. By providing a place to transiently collect fluid, reservoir 61 can allow the rate of suctioning (i.e., draining, aspirating) to be separated from rate of reinfusing. Typically, the rate of reinfusion occurs at substantially the same rate of auctioning, as the volume of fluid suctioned from the site of interest gets immediately directed along the system 1 and introduced right back to the reinfusion site in a patient. However, the availability of a volume of transiently collected fluid in reservoir 61 now provides a source from which the amount or volume of fluid being reinfused back into the patient can be adjusted, for example, to be less than that being suctioned from the site of interest, as well as the rate at which fluid can be reinfused back into the patient, for example, at a relatively slower rate in comparison to the rate of auctioning. Of course, if so desired or necessary, the reinfusion rate and volume can be adjusted to be higher, relative to the rate and volume of suction.

In accordance with one embodiment of the present invention, reservoir 61 may be a closed or an open container, and may be made from a biocompatible material. In an embodiment where reservoir 61 may be a closed container, system 1, likewise, will be a closed system. As a result, pump 15 may be used as both a suction source and a driving force to move fluid from the site of interest to the reinfusion site. In such an embodiment, pump 15 can generate a suction force independently of or alternately with a driving force to allow reservoir 61 collect filtered fluid from filter device 14. In one embodiment, pump 15 may be provided with a gauge in order to measure a rate of flow of the fluid being reinfused.

Alternatively, where reservoir 61 may be an open container, reservoir 61, in such an embodiment, may be designed to accommodate both a volume of fluid, typically at the bottom of reservoir 61, and a volume of air, typically at the top of reservoir 61, to provide an air-fluid interface within reservoir 61. As a result, using pump 15 in fluid communication with reservoir 61 may not provide the needed driving force and/or suction force to adequately remove the undesirable material and to subsequent reinfuse fluid back into a patient. To address this, system 1, in an embodiment, may include a separate and independent vacuum source, in fluid communication with the volume of air at the top of reservoir 61, for providing the necessary suction force from the top area of reservoir 61 where air exists, through filter device 14, through the distal end 11 of cannula 10, and to the site of interest. A port provided above the fluid level within reservoir 61 may be provided to allow the independent vacuum source to be in fluid communication with the volume of air within reservoir 61. Pump 15, on the other hand, may be in fluid communication with the volume of fluid within reservoir 61, and may act to generate the necessary driving force for reinfusion purposes.

It should be appreciated that although shown as separate components, to the extent desired, reservoir 61 and filter device 14 may be combined as a single unit.

Still referring to FIG. 6, system 1 may further include a second filter device 62 positioned in fluid communication between pump 15 and reinfusion cannula 16. Second filter device 62 may act to remove any debris or material (e.g., ranging from smaller than microscopic in size to relatively larger) that may have escaped and moved downstream from filter device 14, so that the fluid may be substantially cleansed prior to reinfusion. In an embodiment, second filter device 62 may include a porous membrane 63 whose pores may be measurably smaller than that in filter device 14, but still capable of allowing fluid to flow therethrough.

Since fluid such as blood needs to be filtered through system 1, it should be noted that system 1 and its components may be made from a biocompatible material to minimize any adverse reaction when fluid removed from the site of interest gets reinfused back into the body.

In operation, system 1 of the present invention may be introduced into the vasculature, preferably through a peripheral blood vessel, to remove undesirable material, such as a clot, emboli, or thrombi, substantially en bloc and without significant fragmentation, and subsequently reinfusing fluid removed from the site of interest back into a patient. In particular, system 1 and its components disclosed above can collectively form a substantially closed circuit through which fluid and an undesirable material from a site of interest can be removed by suction, cleared of the undesirable material, filtered to remove any additional debris, and actively introduced back into a patient at a reinfusion site.

Figure 7:
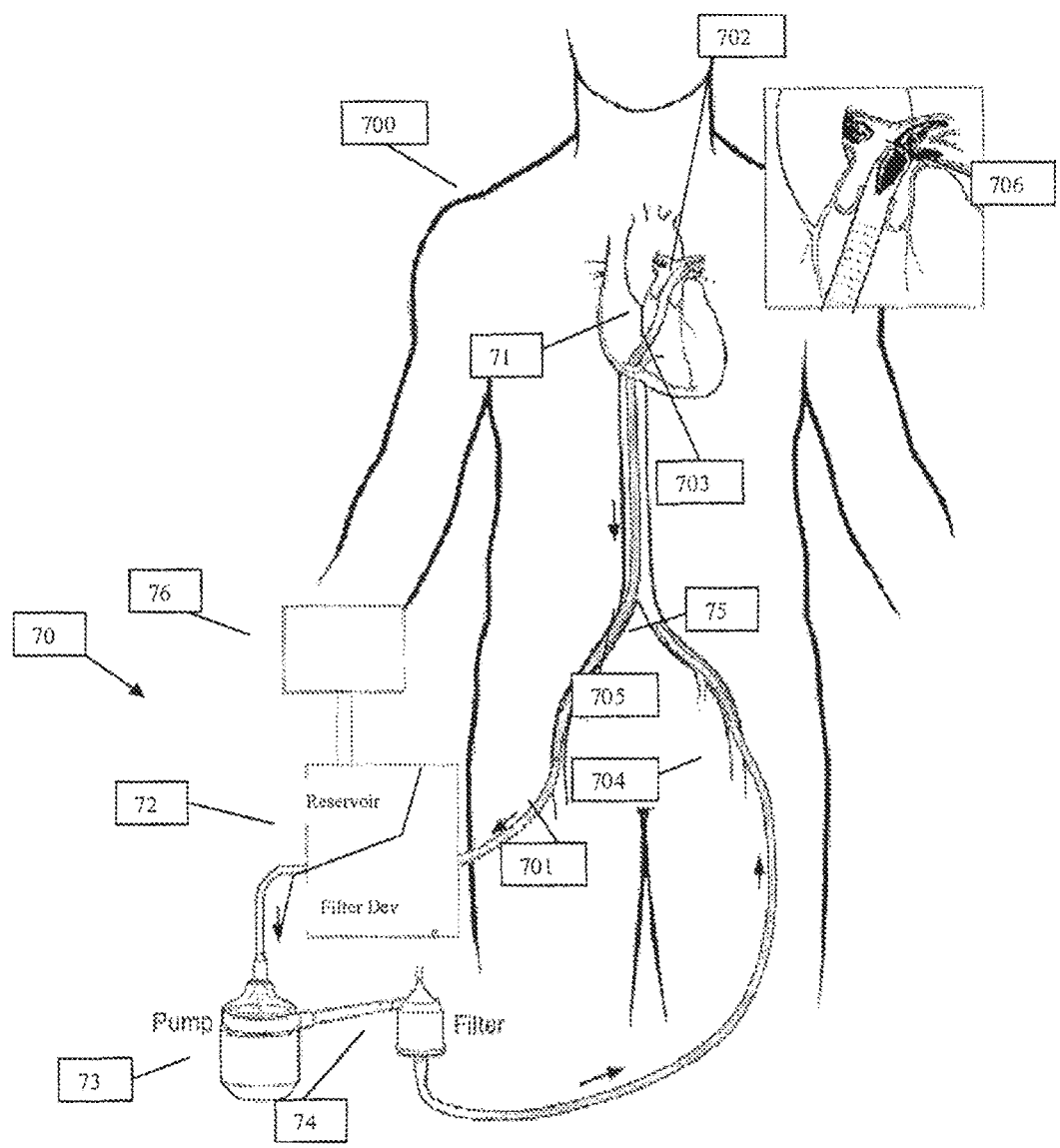
FIG. 7 illustrates a system of the present invention being deployed within a patient for removing an undesirable material from a site of interest.

With reference now to FIG. 7, there is shown one embodiment of the system of the present invention being utilized for removal of an undesirable material within a patient 700. System 70, as illustrated, includes a suction cannula 71, filter device 72, pump 73, second filter device 74 and reinfusion cannula 75. It should be appreciated that depending on the procedure and to the extent desired, system 70 may not need all of the components shown, or may need other components in addition to those shown.

In general the method of the present invention, in one embodiment, includes, initially accessing a first blood vessel 701 either by surgical dissection or percutaneously with, for instance, a needle and guide wire. The first blood vessel through which suction cannula 71 may be inserted into patient 700 can be, in an embodiment, any blood vessel that can be accessed percutaneously or by surgical dissection such as femoral vein, femoral artery or jugular vein. Next, suction cannula 71 may be inserted into the first blood vessel 701 over the guide wire, and advanced toward a site of interest 702, for instance, in a second vessel or a heart chamber 703 where an undesirable material 706 may be residing. The second blood vessel or heart chamber, in an embodiment, can be the main pulmonary artery, branch pulmonary arteries, inferior vena cavae, superior vena cavae, deep veins of the pelvic, legs, arms or neck, aorta, or any other medium to large blood vessel for which the use of a cannula is suitable for removing undesirable material without causing undesirable damage to the blood vessel. In addition, the advancement of suction cannula 71 may be gauged or documented by fluoroscopic angiography, echocardiography or other suitable imaging modality.

In the case of pulmonary embolism, the suction cannula 71 may normally be introduced through the femoral, jugular or subclavian vein. Alternatively, the suction cannula 71 may be introduced, if desired, directly into the cardiac chambers using a minimally invasive surgical or endoscopic, thoracoscopic, or pericardioscopic approach.

Thereafter, a third blood vessel 704 may be accessed either by surgical dissection or percutaneously with, for example, a needle and guide wire. Subsequently, reinfusion cannula 75 may be inserted into the third blood vessel 703 using an open or over the guide wire technique. The third blood vessel through which the reinfusion cannula 75 may be inserted, in one embodiment, can be any large vein, such as the femoral vein or jugular vein. Reinfusion cannula 75 may then be advanced toward a reinfusion site, for example, within a fourth blood vessel 705. The fourth blood vessel, in one embodiment, can be the femoral vein, iliac vein, inferior vena cava, superior vena cava or right atrium.

Once reinfusion cannula 75 is in place and components of system 70 have connected, pump 73 may be activated, and suction cannula 71 may then be placed against and in substantial engagement with the undesirable material 706 at the site of interest 702 for removal by suctioning through the suction cannula 71. The undesirable material 706 and circulatory fluid removed from the site of interest 702 may thereafter be directed along suction cannula 71 into filter device 72 where the undesirable material 706 can be entrapped and removed from the fluid flow. The resulting filtered fluid may next be directed downstream by way of pump 73 into the second filter device 74, where any debris or material (e.g., ranging from smaller than microscopic in size to relatively larger) that may have escaped and moved downstream from filter device 74 can be further captured and removed from the fluid flow prior to reinfusion. The resulting cleansed fluid may then be directed into the reinfusion cannula 75 and introduced back into the patient 700.

It should be appreciated that in certain instances, prior to connecting the suction cannula 71 and the reinfusion cannula 75, system 70 may need to be primed with fluid to minimize or eliminate any air and/or air bubbles from the system prior to the initiation of suction and reinfusion. To that end, the suction cannula 71 and reinfusion cannula 75 can be primed separately with fluid or by allowing blood to backfill the cannula after insertion. The remaining components of the system 70 including all tubing, the filter device 72, the pump 73 and any other components of system 70 may also need to be primed with fluid prior to connecting them to the cannula. In one embodiment, this can be achieved by temporarily connecting these components in fluid communication with other as a closed circuit and infusing fluid through a port, similar to port 51 in FIG. 5, while providing another port through which air can be displaced. Once these components have been fully primed with fluid, the circuit can be detached and connected to the primed suction cannula 71 and reinfusion cannula 75 in the appropriate configuration. Examples of a priming fluid include crystalloid, colloid, autologous or heterologous blood, among others.

During operation, pump 73, in one embodiment, may remain activated so that suction and continuous reinfusion of blood can occur continuously for a desired duration or until the removal of the undesirable material has been confirmed, for instance, by visualizing the captured undesirable material in the filter device 72. Alternatively pump 73 can be activated intermittently in short pulses, either automatically or manually by an operator (e.g., surgeon, nurse or any operating room attendant), for a desired duration or until the removal of the undesirable material has been confirmed by visualization of the material within filter device 72.

It should be appreciated that since suction cannula 71 may be deployed within any vessel within patient 700, depending on the procedure, in addition to being placed substantially directly against the undesirable material at the site of interest, suction cannula 71 may be deployed at a location distant from the site of interest where direct engagement with the undesirable material may not be possible or desired.

In a situation where the suction cannula 71 is positioned within a vessel exhibiting a venous flow and at a distant location from the undesirable material, it may be desirable to place the distal end of suction cannula 71 downstream of the undesirable material, so that the fluid flow can push the undesirable material from the site of interest into suction cannula 71 during suction. To the extent there may be some difficulties with suctioning the undesirable material from its location, if necessary, a catheter may be deployed through suction cannula 71 and to the site of interest, where the undesirable material may be dislodged location for subsequent removal.

On the other hand, when suction cannula 71 is positioned within a vessel exhibiting arterial flow and at a distant location from the undesirable material, it may be necessary to place the distal end of suction cannula 71 upstream of the undesirable material for the purposes of removal, even though the undesirable material must move against the fluid flow in order to enter into the suction cannula 71. In such a situation, since the fluid flow in the vessel tends to exert a pressure against the undesirable material at the site of interest, and thus may make the undesirable material difficult to remove, suction cannula 71 may include a flow occlusion mechanism, similar to balloon 33 shown in FIG. 3. When expanded radially, the mechanism can substantially occlude the vessel, such that pressure being exerted on the downstream material by the fluid flow can be lessened. By lessening the pressure on the undesirable material to be removed, the suction force being applied at the site of interest can act to remove the material more easily. Again, if necessary, a catheter may be deployed through suction cannula 71 and to the site of interest, where the undesirable material may be dislodged or drawn back into the cannula to facilitate its removal.

The method of the present invention may also utilize a fluid reservoir, similar to reservoir 61 shown in FIG. 6, in connection with system 70. Such a reservoir may be placed in fluid communication between filter device 72 and pump 73. The reservoir, in an embodiment, may be an independent reservoir or may be integrated with filter device 72 as a single unit, similar to that shown in FIG. 7. By utilizing a reservoir, a volume of transiently collected fluid may be used to independently control the rate or volume of suctioning (i.e., draining, aspirating) and/or the rate or volume of reinfusion.

In an embodiment where the reservoir may be an open container, it should be appreciated that system 70 may not be a substantially closed system. As a result, rather than utilizing a pump that can generate both a suction and a driving force for a closed system, an independent vacuum device 76 may be employed to generate the necessary suction force, from the top of the reservoir where a volume of air exists, for removal of the undesirable material, while independent pump 73 may be employed to generate the necessary driving force, from the bottom of the reservoir where a volume of aspirated fluid exists, for reinfusion.

The method of the present invention may also utilize a suction cannula 71 with a deployable funnel tip, similar to funnel 20 in FIG. 2 or in FIG. 3. In such an embodiment, the funnel may be deployed after suction cannula 71 has been positioned adjacent the site of interest. Thereafter, once the suction force has been activated, the funnel may be advanced to engage the undesirable material for removal. The funnel may remain deployed while the suction force is activated, continuously or through multiple cycles, if necessary, until the undesirable material can be removed. Subsequently, the funnel may be retracted in order to reposition or remove suction cannula 71.

The method of the present invention may further utilize reinfusion cannula 75 that has been incorporated into an introducer sheath, such as sheath 43 as a multi-lumen cannula (FIG. 4C) or as one which concentrically aligns the suction cannula and reinfusion cannula (FIG. 4D). In this embodiment, the sheath/reinfusion cannula 75 may initially be inserted into a first blood vessel. Suction cannula 71 may then be inserted into the introducer lumen of the sheath/reinfusion cannula 75, and the assembly advanced together to a site of interest in a second blood vessel or heart chamber.

The method of the present invention may also further utilize a combined multi-lumen suction/reinfusion cannula, similar to cannula 46 shown in FIG. 4E. In such an embodiment, the combined suction/reinfusion cannula may initially be inserted into a first blood vessel to a location where its distal suction lumen can be placed adjacent the site of interest within a second blood vessel, while its proximal located reinfusion lumen can be positioned at an appropriately spaced location from the suction lumen.

The method of the present invention may, in an embodiment, be employed to remove a plurality of undesirable materials, for instance, within the same vessel or its branches, from multiple vessels within the same vascular bed (e.g. left and right pulmonary arteries), from different vascular beds (e.g. pulmonary artery and iliofemoral veins), or a combination thereof. In such an embodiment, after the first undesirable material has been removed, the suction force may be deactivated. The next undesirable material to be removed may then be located, for example, using an appropriate imaging modality. Suction cannula 71 may thereafter be advanced to the location of this second undesirable material, and the suction force reactivated as above until this second undesirable material may be removed. The cycle may be repeated until each undesirable material at the various identified locations has been removed. Once all undesirable material has been removed, an appropriate procedure to prevent the development of or migration of new material, such as placement of an inferior vena cava filter, may be performed.

The method of the present invention may also be employed in combination with a balloon embolectomy catheter or other devices suitable for dislodging clots or other undesirable material from a cannula or a vessel. For example, should an undesirable material be lodged within suction cannula 71, a balloon catheter can be inserted through, for instance, a side port, similar to port 51 in FIG. 5, of suction cannula 71 and advanced past the lodged undesirable material. The balloon catheter may subsequently be inflated distal to the undesirable material. Once inflated, the suction force may be activated and the inflated catheter withdrawn along the suction cannula 71 to dislodge the undesirable material from its location of obstruction. In a situation where the undesirable material may be adherent to a vessel wall, or for some other reason cannot be dislodged by simply applying suction to the site of interest, the balloon catheter can be inserted through the side port of suction cannula 71, advanced past a distal end of cannula 71, and past the adherent undesirable material. The balloon catheter may then be inflated distal to the undesirable material. Once inflated, the suction force may be activated and the inflated catheter withdrawn along the suction cannula 71. As it is withdrawn, the balloon catheter can act to drag the undesirable material into suction cannula 71.

Figure 8:
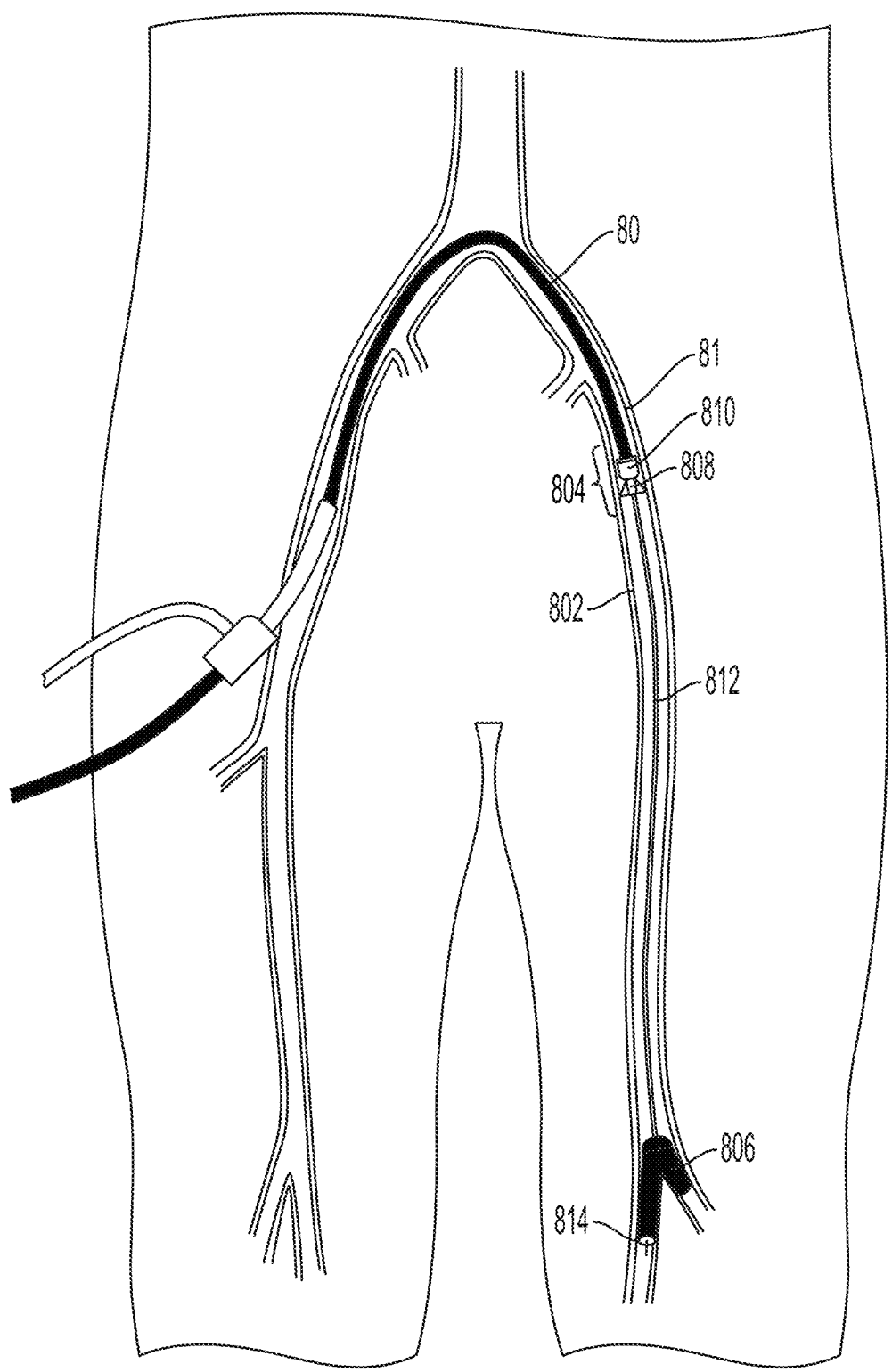
FIG. 8 illustrates a system of the present invention being deployed within a patient for removing an undesirable material from a site of interest.

For example, turning to FIG. 8, the present invention may be used to dislodge undesirable material from a blood vessel by utilizing a balloon catheter. Undesirable material 806 may, for example, adhere to vessel 802 so that the suction force provided by suction cannula 80 is insufficient to dislodge undesirable material 806 from vessel 802 without an additional force being applied.

In FIG. 8, suction cannula 80 is shown deployed within vessel 802 of a patient. Suction cannula 80 may be a cannula, as described above, designed to create a suction force within vessel 802 for removal of undesirable material 806. Suction cannula may be deployed proximal or adjacent to undesirable material 802, or, as shown in FIG. 8, at a position 804 relatively distant from undesirable material 806. Suction cannula 80 may include a funnel 808 and balloon 810, as described in detail above. When engaged, suction cannula 80 may produce a suction force within vessel 802 for capturing and removing undesirable material 806.

The system may also include catheter 812. Catheter 812 may be designed to be extended from a lumen, side port, or other pathway within suction cannula 80. Catheter 812 may also be designed to push through or push past undesirable material 806. Accordingly, catheter 812 may be made from a material sufficiently stiff in the lateral direction to push through or past undesirable material without folding or buckling. As one skilled in the art will recognize, catheter 812 may also be made from a material sufficiently pliable, for example, radially, to be directed and maneuvered through the circulatory system of a patient.

Balloon 814, as illustrated, may be coupled or bonded to catheter 812. The bonding may be sufficiently strong to that, if balloon 814 and/or catheter 812 are used to exert a force upon undesirable material 806, balloon 814 will not become dislodged from catheter 812. In one embodiment, balloon 814 and catheter 812 may be separate parts coupled together by an adhesive(s), fastener(s), or any other method of coupling known in the art. In another embodiment, balloon 814 and catheter 812 may comprise a single part. For example, balloon 812 and catheter 812 may come from a single part from a single plastic mold used during construction of balloon 814 and catheter 812. One skilled in the art will recognize that balloon 814 and catheter 812 may be bonded or constructed in any way that allows balloon 814 to remain attached to catheter 812 after balloon 814 exerts a force upon undesirable material 806.

Upon activation, balloon 814 may be inflated to a size sufficient to partially or completely occlude the flow of blood or other fluids through vessel 802. When deflated, balloon 814 may have a diameter sufficiently small so that balloon 814 can be pushed past or through undesirable material 814. Catheter 812 may have an internal lumen, and may be designed to pump fluid, i.e. a gas or liquid, into and out of balloon 814 in order to inflate and deflate balloon 814 through the internal lumen, for example. One skilled in the art will recognize that other methods of inflating and deflating the balloon are also within the scope of the invention.

Although not shown in FIG. 8, the system may also include a reinfusion cannula, such as reinfusion cannula 16 shown in FIG. 1, for example. The reinfusion catheter may return blood and other fluids that were removed by suction cannula 80 to the body. As described above, catheter 812 may also be designed to be extended from a lumen of the reinfusion cannula.

The system may be employed to utilize catheter 812 and/or balloon 814 to dislodge undesirable material 806 vessel 802. One skilled in the art will appreciate that the system may also be used to remove undesirable material 806 from other types of blood vessels, from chambers of the heart, from valves of the heart, etc.

As shown in FIG. 8, the distal end 11 of suction cannula 10 may be positioned within vessel 802 at location 804. Location 804 may be spatially distant from undesirable material 806. In some situations, it may be advantageous to position cannula 80 at a position that is spatially distant from undesirable material 806. For example, in some situations, cannula 80 may not be long enough to reach from its point of insertion in the patient's body to the location of undesirable material 806. In another example, it may be in the best interest of the patient, for various health reasons, to position cannula 80 at a distant position from undesirable material 806 within the body. In yet another example, it may be difficult or impossible to maneuver cannula 80 through vessel 802 to a position adjacent to undesirable material 806. There may also be various other reasons for positioning cannula 80 at a position distant to undesirable material 806. Of course, one skilled in the art will recognize that the opposite may also be true. For example, cannula 80 may be placed at a position close or adjacent to undesirable material 806, and/or may be placed at a position upstream of undesirable material 806.

As shown in FIGS. 1 and 7 and described above, reinfusion cannula 16 may be placed within a blood vessel, in fluid communication with suction cannula 80, to provide reinfusion of fluid into the patient's body. Typically, the reinfusion cannula may be situated in a position downstream of undesirable material 806. However, if suction cannula 80 is placed upstream of undesirable material 806, reinfusion cannula 16 may also be positioned upstream of undesirable material 806.

Suction cannula 80 may operate to provide a suction force within vessel 802. During operation, the suction force may result in removal of at least some of the patient's blood and other fluids from vessel 802. As discussed above, reinfusion cannula 16 may reinfuse the blood and/or other fluids into the body. In some embodiments, the force exerted on undesirable material 806 by the suction may be sufficient to dislodge undesirable material 806 from vessel 802. In such a case, undesirable material 802 may become dislodged from its position, and may travel along vessel 802 to be captured by suction cannula 80 and removed from the patient.

In other cases, even in the presence of the suction force created by suction cannula 80 and/or the reinfusion of fluid from reinfusion cannula 16, the suction and reinfusion forces within vessel 802 may be insufficient to dislodge undesirable material 806 from its position. In such cases, it may be desirable to increase the force applied to undesirable material 806 and/or exert an additional force upon undesirable material 806 in order to dislodge and capture it.

Catheter 812 and/or balloon 814 may be used to impart a force on undesirable material 806 in order to dislodge it from its location. In an embodiment, catheter 812 and/or balloon 814 may be used to pull undesirable material 806 from its position within vessel 802. In such embodiment, catheter 812 may be extended from distal end 81 of suction cannula 80 to engage undesirable material 806. Although not shown in FIG. 8, catheter 812 may also be extended from the distal end of reinfusion cannula 16.

Once extended, catheter 812 may be maneuvered so that it passes through or past undesirable material 806. For example, catheter 812 may be pushed through undesirable material 806, or may be pushed between undesirable material 806 and the wall of vessel 802. Catheter 812 may be maneuvered in this way until, for example, undesirable material 806 is situated between balloon 814 and the distal end 81 of cannula 80. Balloon 814 may be deflated while catheter 812 is pushed through or past undesirable material 806, thus reducing its diameter so that it may pass through or past undesirable material more easily.

Once catheter 812 is through or past undesirable material 806, balloon 814 may be inflated. Accordingly, undesirable material 802 may be situated between inflated balloon 814 and distal end 81 of suction cannula 80.

After balloon 814 is inflated, suction cannula 80 may be engaged to provide a suction force within vessel 802. If the suction force is not sufficient to dislodge and capture undesirable material, catheter 812 and balloon 814 may provide a pulling force on undesirable material 806 as shown by arrow 816. Once balloon 814 has been pushed through or past undesirable material 806 and subsequently inflated, balloon 814 may be used to exert a pulling force on undesirable material 806. If catheter 812 is pulled back toward cannula 80, the surface of balloon 814 proximal to undesirable material 806 may engage undesirable material 806 and exert a pulling force. The pulling force may partially or completely dislodge undesirable material 806 from its position within vessel 802.

As mentioned above, suction cannula 80 may be engaged to provide a suction force within vessel 802. Once undesirable material is dislodged by catheter 812 and balloon 814, the suction force may capture undesirable material 806 and remove it from vessel 802. In some cases, undesirable material may be carried into suction cannula 80 by the suction force provided. However, in other cases, if catheter 812 has been pushed through undesirable material 806, catheter 812 and balloon 814 may engage undesirable material 806 and pull it back into the distal end 81 of suction cannula 80 for capture and removal.

Although the example above describes operation with a balloon catheter, other devices may be used to dislodge the undesirable material and/or push, pull, or anchor the undesirable material 806 in order to dislodge it from vessel 802. For example, instead of a balloon catheter, another thrombectomy device, e.g. a rheolytic thrombectomy catheter, a fragmentation thrombectomy catheter, an aspiration thrombectomy catheter, etc.

In another embodiment, catheter 812 and balloon 814 may be used to flush undesirable material 904 from its position in vessel 802. FIG. 8 shows catheter 812 extended from suction catheter 80 and pushed through or past undesirable material 806, as described above. Once catheter 812 is positioned past undesirable material 806, balloon 814 may be inflated. As shown, balloon 814 may be situated so that undesirable material 806 is between balloon 814 and distal end 81 of suction catheter 80. When inflated, balloon 814 may have a diameter sufficient to partially or completely occlude the flow of blood and other fluid in vessel 802. The partial or complete blockage vessel 802 may be utilized to provide a flushing force upon undesirable material 806 to dislodge it from its position in vessel 802.

Once balloon 814 is inflated, suction cannula 80 may be engaged to provide a suction force within vessel 802. By occluding vessel 802, inflated balloon 814 may allow the suction force to build up within vessel 802 to create a greater negative pressure that otherwise would be created. Once there has been sufficient time for the negative pressure to build, balloon 814 may be deflated. As balloon 814 is deflated, it will no longer occlude the flow of blood and other fluid within vessel 802. As a result, because of the increased suction force, fluid may rush into area (from, for example, the reinfusion cannula or other areas of vessel 802) to equalize the negative pressure caused by the suction force. The rush of fluid may create a flushing action that may dislodge undesirable material 806 from vessel 802. In some cases, the negative pressure and/or the fluid flowing into area may distend the walls of vessel 802 or otherwise cause the shape of vessel 802 to temporarily change. The change in shape and/or stretching and contraction of the walls of vessel 802 may also help to dislodge undesirable material 806.

If the initial flushing does not dislodge undesirable material 806, the process may be repeated as many times as necessary to dislodge undesirable material 806. Balloon 814 may be inflated and deflated repeatedly to create an alternating flushing/suction force that may act upon undesirable material 806. Balloon 814 may be inflated and deflated rapidly or slowly. Similarly, the time allowed for the suction force to build up within vessel 802 may be varied by inflating and deflating balloon 814 to allow for a greater suction force and/or a more frequent flushing force, as the circumstances warrant. Varying the strength and frequency of the flushing force by inflating and deflating balloon 814 may assist in dislodging undesirable material 806 from vessel 802.

The method of the present invention may further be employed in combination with a distal protection device (not shown), such as a netting device, designed to be positioned downstream of the undesirable material, when removal may be performed within a vessel having arterial flow. In particular, with suction cannula 71 positioned upstream of the undesirable material, the netting device may be inserted through a side port in suction cannula 71, advanced past the undesirable material to a downstream location. The netting device may then be deployed to an open position approximating the diameter of the vessel. The deployed netting device may then act to entrap any material that may be dislodged from the site of interest and pushed downstream by the fluid flow. In the absence of the netting device, a dislodged material may be pushed downstream and may be lodged in a more life threatening location.

It is evident from the above description that the systems, including the various components, and methods of the present invention can act to remove clots and other types of undesirable material from the circulation, particularly from medium to larger vessels and heart chambers. Important to achieving this includes the ability of the operator to perform substantially en bloc removal of the undesirable material without significant fragmentation from the site of interest. Such a protocol may only be achieved previously with invasive, open surgery. In addition, by providing a system with components to permit aspirated fluid from the site of interest to be reinfused back to the patient, the system of the present invention allows a sufficiently and relatively large suction cannula to be employed for the removal of a relatively large undesirable material 15 in substantially one piece, without fragmentation. Furthermore, by providing a definitive mechanical treatment to the problem, the systems and methods of the present invention provide an attractive alternative to treatments, such as thrombolysis, which may not be an option or may be ineffective for many patients, and which may carry a significant risk of major complications. As such, the systems and methods of the present invention now provide a significant contribution to the field of cardiovascular medicine and surgery, particularly thromboembolic disease.

Although references have been made in connection with surgical protocols, it should be appreciated that the systems and methods of the present invention may be adapted for use in connection with non-surgical protocols, and in connection with any vessel capable of permitting fluid flow therethrough and capable of being obstructed. For instance, the system of the present invention may be adapted for use in connection with clearing obstructed oil pipelines, water pipes, and air ducts, among others.

While the present invention has been described with reference to certain embodiments thereof it should be understood by those skilled in the art that various changes may be made and equivalents may be substituted without departing from the true spirit and scope of the invention. In addition, many modifications may be made to adapt to a particular situation, indication, material and composition of matter, process step or steps, without departing from the spirit and scope of the present invention. All such modifications are intended to be within the scope of the following claims.

What is claimed is:

1. A method for treatment of undesirable material within a vasculature of a body, the method comprising:
    placing at least a portion of an aspiration cannula at least partially within the vasculature;
    aspirating at least a portion of the undesirable material and blood through the aspiration cannula and into a reservoir coupled to the aspiration cannula;
    coupling the reservoir in fluid communication with a filter assembly and a pump;
    driving the portion of the undesirable material and the aspirated blood from the reservoir through the filter assembly into the pump, wherein the filter assembly is configured to filter the portion of the undesirable material from the aspirated blood to produce filtered blood;
    coupling the pump in fluid communication with a reinfusion cannula at least partially positioned within the vasculature; and
    driving the filtered blood from the pump through the reinfusion cannula into the vasculature.

2. The method of claim 1, further comprising:
    placing a secondary device coaxially through a lumen of the aspiration cannula; and
    dislodging at least a portion of the undesirable material with an expandable element coupled to a distal end of the secondary device.

3. The method of claim 1, wherein the pump is a manually operated pump.

4. The method of claim 3, wherein the reservoir is configured to collect the total volume of undesirable material and the blood aspirated through the aspiration cannula.

5. The method of claim 4, wherein the reservoir is a closed container.

6. The method of claim 5, wherein the aspiration cannula and the reinfusion cannula comprise a single multi-lumen catheter.

7. The method of claim 5, wherein the aspiration cannula and the reinfusion cannula comprise separate catheters.

8. The method of claim 7, wherein a rate of aspiration of the undesirable material and blood through the aspiration cannula is different than a rate of reinfusion of the filtered blood through the reinfusion cannula.

9. The method of claim 7, wherein the aspiration cannula and the reinfusion cannula are placed in different locations within the vasculature.

10. A method for treatment of clot material within a vasculature of a body, the method comprising:
    placing at least a portion of a suction cannula at a treatment site;
    aspirating at least a portion of the clot material and blood through the suction cannula and into a container coupled to the suction cannula;
    coupling the container in fluid communication with a filter assembly and a pump;
    driving the portion of the clot material and aspirated blood from the container through the filter assembly into the pump, wherein the filter assembly is configured to filter the portion of the clot material from the aspirated blood to produce filtered blood;
    coupling the pump in fluid communication with a reinfusion cannula at least partially positioned within the vasculature; and
    driving the filtered blood from the pump through the reinfusion cannula into the vasculature.

11. The method of claim 10, wherein the reinfusion cannula is an introducer sheath, and wherein the suction cannula is configured to be coaxially placed through a lumen of the reinfusion cannula.

12. The method of claim 11, further comprising:
    placing a secondary device coaxially through the suction cannula; and
    dislodging at least a portion of the clot material with an expandable element coupled to a distal end of the secondary device.

13. The method of claim 10, wherein aspirating at least a portion of the clot material and blood through the suction cannula and into the container comprises activating a manually operated pump coupled to the suction cannula and the container, wherein the manually operated pump is configured to generate an aspiration force through the suction cannula.

14. The method of claim 12, further comprising
    advancing the secondary device distal to the clot material;
    expanding the expandable element; and
    retracting the secondary device proximally towards the suction cannula.

15. A method for treatment of undesirable material within a vasculature of a body, the method comprising:
    placing a first cannula at a treatment site within the vasculature;
    placing a secondary device coaxially through a lumen of the first cannula and within the vasculature distal to the undesirable material;
    expanding an expandable element coupled to a distal end of the secondary device;
    disrupting at least a portion of the undesirable material by engaging at least a portion of the undesirable material with the expandable element;
    aspirating at least the portion of the undesirable material that was disrupted by the expandable element and blood through the first cannula and into a first container coupled to the first cannula;
    coupling the first container in fluid communication with a filter assembly and a second container;
    driving the portion of the undesirable material and the aspirated blood from the first container through the filter assembly into the second container, wherein the filter assembly is configured to filter the portion of the undesirable material from the aspirated blood to produce filtered blood;
    coupling the second container in fluid communication with a second catheter at least partially positioned within the vasculature; and
    driving the filtered blood from the second container through the second catheter into the vasculature.

16. The method of claim 15, wherein the first container is configured to transiently collect the aspirated undesirable material and blood prior to being filtered.

17. The method of claim 16, wherein the second container includes a pump and the pump is configured to be manually operated.

18. The method of claim 17, further comprising:
    placing the first cannula at a second treatment site within the vasculature.

19. The method of claim 17, wherein the expandable element comprises a netting device configured to entrap the undesirable material.

20. The method of claim 17, wherein the expandable element comprises a fragmentation thrombectomy device configured to fragment the undesirable material.

* * * * *